United States Patent
Barry et al.

(10) Patent No.: US 11,992,248 B2
(45) Date of Patent: May 28, 2024

(54) INTRAMEDULLARY IMPLANT AND METHOD OF USE

(71) Applicant: Stryker European Operations Holdings LLC, Kalamazoo, MI (US)

(72) Inventors: David Barry, New York, NY (US); Manoj Kumar Singh, Mahwah, NJ (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 300 days.

(21) Appl. No.: 17/666,759

(22) Filed: Feb. 8, 2022

(65) Prior Publication Data

US 2022/0160407 A1    May 26, 2022

Related U.S. Application Data

(63) Continuation of application No. 16/587,793, filed on Sep. 30, 2019, now Pat. No. 11,272,966, which is a
(Continued)

(51) Int. Cl.
*A61B 17/84* (2006.01)
*A61B 17/70* (2006.01)
(Continued)

(52) U.S. Cl.
CPC ...... *A61B 17/7291* (2013.01); *A61B 17/7098* (2013.01); *A61B 17/72* (2013.01);
(Continued)

(58) Field of Classification Search
CPC ................ A61B 17/7291; A61B 17/7098
See application file for complete search history.

(56) References Cited

U.S. PATENT DOCUMENTS

| 321,389 A | 6/1885 | Schirmer |
|---|---|---|
| 1,095,054 A | 4/1914 | Wiesenfeld |

(Continued)

FOREIGN PATENT DOCUMENTS

| CA | 2551021 A1 | 3/2005 |
|---|---|---|
| CA | 2243699 C | 1/2006 |

(Continued)

OTHER PUBLICATIONS

EP Notification for Application No. 09741356.1 dated Feb. 12, 2015, 4 pages.

(Continued)

*Primary Examiner* — Christian A Sevilla
(74) *Attorney, Agent, or Firm* — Lerner David LLP

(57) ABSTRACT

A bone implant includes a proximal end, a distal end, a first portion extending between the proximal and distal ends having a maximum and minimum portion height, and a second portion extending between the proximal and distal ends having a maximum and minimum portion height. The second portion is connected to the first portion at the proximal end and the distal end and at least one of the first portion and the second portion is moveable relative to the other of the first portion and the second portion so as to transition the bone implant between a relaxed state wherein the first and second portions are separated by a first distance and a contracted state wherein the first and second portions are separated by a second distance different from the first distance. At least one of the proximal end and the distal end have the minimum portion height.

20 Claims, 39 Drawing Sheets

Related U.S. Application Data continuation of application No. 15/612,733, filed on Jun. 2, 2017, now Pat. No. 10,470,807.

(60) Provisional application No. 62/399,838, filed on Sep. 26, 2016, provisional application No. 62/345,517, filed on Jun. 3, 2016.

(51) Int. Cl.
*A61B 17/72* (2006.01)
*A61B 17/88* (2006.01)
*A61F 2/30* (2006.01)

(52) U.S. Cl.
CPC ......... *A61B 17/7258* (2013.01); *A61B 17/84* (2013.01); *A61B 17/885* (2013.01); *A61B 17/8872* (2013.01); *A61F 2/30767* (2013.01)

(56) References Cited

U.S. PATENT DOCUMENTS

| | | |
|---|---|---|
| 1,517,334 A | 12/1924 | Young |
| 1,893,864 A | 1/1933 | Kocher |
| 2,580,821 A | 1/1952 | Nicola |
| 2,984,248 A | 5/1961 | Sidelman |
| 3,462,765 A | 8/1969 | Swanson |
| 3,466,669 A * | 9/1969 | Flatt ............... A61F 2/4241 623/21.17 |
| 3,593,342 A | 7/1971 | Niebauer et al. |
| 3,681,786 A | 8/1972 | Lynch |
| 3,739,403 A | 6/1973 | Nicolle |
| 3,805,302 A | 4/1974 | Mathys |
| 3,824,631 A | 7/1974 | Burstein et al. |
| 3,875,594 A | 4/1975 | Swanson |
| D243,716 S | 3/1977 | Treace et al. |
| 4,091,806 A | 5/1978 | Aginsky et al. |
| 4,158,893 A | 6/1979 | Swanson |
| 4,204,284 A | 5/1980 | Koeneman |
| 4,276,660 A | 7/1981 | Laure |
| 4,364,382 A | 12/1982 | Mennen |
| 4,367,562 A | 1/1983 | Gauthier et al. |
| 4,485,816 A | 12/1984 | Krumme |
| D277,509 S | 2/1985 | Lawrence et al. |
| D277,784 S | 2/1985 | Sgarlato et al. |
| 4,522,200 A | 6/1985 | Stednitz |
| D284,099 S | 6/1986 | Laporta et al. |
| 4,634,382 A | 1/1987 | Kusano et al. |
| D291,731 S | 9/1987 | Aikins |
| 4,759,768 A | 7/1988 | Hermann et al. |
| 4,871,367 A | 10/1989 | Christensen et al. |
| 4,905,679 A | 3/1990 | Morgan |
| 4,955,916 A | 9/1990 | Carignan et al. |
| 4,969,909 A | 11/1990 | Barouk |
| 5,011,497 A | 4/1991 | Persson et al. |
| 5,047,059 A | 9/1991 | Saffar |
| 5,062,851 A | 11/1991 | Branemark |
| 5,074,865 A | 12/1991 | Fahmy |
| 5,092,896 A | 3/1992 | Meuli et al. |
| 5,108,443 A | 4/1992 | Branemark |
| 5,133,761 A | 7/1992 | Krouskop |
| 5,179,915 A | 1/1993 | Cohen et al. |
| 5,190,546 A | 3/1993 | Jervis |
| 5,207,712 A | 5/1993 | Cohen |
| 5,326,364 A | 7/1994 | Clift, Jr. et al. |
| 5,360,450 A | 11/1994 | Giannini |
| 5,405,400 A | 4/1995 | Linscheid et al. |
| 5,405,401 A | 4/1995 | Lippincott, III et al. |
| 5,417,692 A | 5/1995 | Goble et al. |
| 5,425,776 A | 6/1995 | Cohen |
| 5,425,777 A | 6/1995 | Sarkisian et al. |
| 5,454,814 A | 10/1995 | Comte |
| 5,464,427 A | 11/1995 | Curtis et al. |
| 5,474,557 A | 12/1995 | Mai |
| D366,114 S | 1/1996 | Ohata |
| 5,480,447 A | 1/1996 | Skiba |
| 5,484,443 A | 1/1996 | Pascarella et al. |
| D369,412 S | 4/1996 | Morgan |
| 5,507,822 A | 4/1996 | Bouchon et al. |
| 5,522,903 A | 6/1996 | Sokolow et al. |
| 5,554,157 A | 9/1996 | Errico et al. |
| 5,578,036 A | 11/1996 | Stone et al. |
| 5,634,925 A | 6/1997 | Urbanski |
| 5,674,297 A | 10/1997 | Lane et al. |
| 5,690,631 A | 11/1997 | Duncan et al. |
| 5,702,472 A | 12/1997 | Huebner |
| D388,877 S | 1/1998 | Morgan |
| 5,725,585 A | 3/1998 | Zobel |
| 5,779,707 A | 7/1998 | Bertholet et al. |
| 5,782,927 A | 7/1998 | Klawitter et al. |
| 5,824,095 A | 10/1998 | Di Maio, Jr et al. |
| 5,876,434 A | 3/1999 | Flomenblit et al. |
| 5,881,443 A * | 3/1999 | Roberts ............... A61F 2/30907 425/111 |
| 5,882,444 A | 3/1999 | Flomenblit et al. |
| 5,919,193 A | 7/1999 | Slavitt |
| 5,951,288 A | 9/1999 | Sawa |
| 5,958,159 A | 9/1999 | Prandi |
| 5,984,970 A | 11/1999 | Bramlet |
| 5,984,971 A | 11/1999 | Faccioli et al. |
| 6,011,497 A | 1/2000 | Tsang et al. |
| 6,017,366 A | 1/2000 | Berman |
| 6,093,188 A | 7/2000 | Murray |
| 6,123,709 A | 9/2000 | Jones |
| 6,146,387 A | 11/2000 | Trott et al. |
| 6,162,234 A | 12/2000 | Freedland et al. |
| 6,187,008 B1 | 2/2001 | Hamman |
| 6,193,757 B1 | 2/2001 | Foley et al. |
| 6,197,037 B1 | 3/2001 | Hair |
| 6,200,330 B1 | 3/2001 | Benderev et al. |
| 6,248,109 B1 | 6/2001 | Stoffella |
| 6,261,289 B1 | 7/2001 | Levy |
| 6,319,284 B1 | 11/2001 | Rushdy et al. |
| 6,325,805 B1 | 12/2001 | Ogilvie et al. |
| 6,342,076 B1 | 1/2002 | Lundborg |
| 6,348,052 B1 | 2/2002 | Sammarco |
| 6,352,560 B1 | 3/2002 | Poeschmann et al. |
| 6,383,223 B1 | 5/2002 | Baehler et al. |
| 6,386,877 B1 | 5/2002 | Sutter |
| 6,395,031 B1 | 5/2002 | Foley et al. |
| 6,423,097 B2 | 7/2002 | Rauscher |
| 6,428,634 B1 | 8/2002 | Besselink et al. |
| 6,454,808 B1 | 9/2002 | Masada |
| 6,475,242 B1 | 11/2002 | Bramlet |
| 6,554,833 B2 | 4/2003 | Levy et al. |
| 6,689,169 B2 | 2/2004 | Harris |
| 6,692,499 B2 | 2/2004 | Tormala et al. |
| 6,699,247 B2 | 3/2004 | Zucherman et al. |
| 6,699,292 B2 | 3/2004 | Ogilvie et al. |
| 6,706,045 B2 | 3/2004 | Lin et al. |
| 6,773,437 B2 | 8/2004 | Ogilvie et al. |
| 6,811,568 B2 | 11/2004 | Minamikawa |
| 6,827,741 B2 | 12/2004 | Reeder |
| 6,833,006 B2 | 12/2004 | Foley et al. |
| 6,869,449 B2 | 3/2005 | Ball et al. |
| 6,896,177 B2 | 5/2005 | Carter |
| 6,981,974 B2 | 1/2006 | Berger |
| 7,025,789 B2 | 4/2006 | Chow et al. |
| 7,037,342 B2 | 5/2006 | Nilsson et al. |
| 7,041,106 B1 | 5/2006 | Carver et al. |
| 7,052,498 B2 | 5/2006 | Levy et al. |
| 7,182,787 B2 | 2/2007 | Hassler et al. |
| 7,240,677 B2 | 7/2007 | Fox |
| 7,291,175 B1 | 11/2007 | Gordon |
| 7,537,664 B2 | 5/2009 | O'Neill et al. |
| 7,588,603 B2 | 9/2009 | Leonard |
| 7,600,956 B2 | 10/2009 | McDuff et al. |
| 7,601,152 B2 | 10/2009 | Levy et al. |
| 7,655,042 B2 | 2/2010 | Foley et al. |
| 7,670,339 B2 | 3/2010 | Levy et al. |
| 7,674,426 B2 | 3/2010 | Grohowski, Jr. |
| 7,780,737 B2 | 8/2010 | Bonnard et al. |
| 7,837,738 B2 | 11/2010 | Reigstad et al. |
| 7,842,091 B2 | 11/2010 | Johnstone et al. |
| 7,909,880 B1 | 3/2011 | Grant |

(56) References Cited

U.S. PATENT DOCUMENTS

| | | |
|---|---|---|
| 7,918,879 B2 | 4/2011 | Yeung et al. |
| 7,922,765 B2 | 4/2011 | Reiley |
| 7,955,388 B2 | 6/2011 | Jensen et al. |
| 7,976,580 B2 | 7/2011 | Berger |
| 7,993,403 B2 | 8/2011 | Foley et al. |
| 8,048,173 B2 | 11/2011 | Ochoa |
| 8,100,983 B2 | 1/2012 | Schulte |
| 8,162,942 B2 | 4/2012 | Coati et al. |
| 8,202,305 B2 | 6/2012 | Reiley |
| 8,262,712 B2 | 9/2012 | Coilard-Lavirotte et al. |
| 8,308,779 B2 | 11/2012 | Reiley |
| 8,388,667 B2 | 3/2013 | Reiley et al. |
| 8,394,097 B2 | 3/2013 | Peyrot et al. |
| 8,414,583 B2 * | 4/2013 | Prandi ............... A61B 17/8605 623/21.19 |
| 8,414,648 B2 | 4/2013 | Reiley |
| 8,425,570 B2 | 4/2013 | Reiley |
| 8,444,693 B2 | 5/2013 | Reiley |
| 8,470,004 B2 | 6/2013 | Reiley |
| 8,475,456 B2 | 7/2013 | Augoyard et al. |
| 8,529,611 B2 | 9/2013 | Champagne et al. |
| 8,597,337 B2 | 12/2013 | Champagne |
| 8,608,785 B2 | 12/2013 | Reed et al. |
| 8,685,024 B2 | 4/2014 | Roman |
| 8,715,325 B2 | 5/2014 | Weiner et al. |
| 8,728,387 B2 | 5/2014 | Jones et al. |
| 8,734,462 B2 | 5/2014 | Reiley et al. |
| 8,734,491 B2 | 5/2014 | Seavey |
| 8,834,483 B2 | 9/2014 | Cheney et al. |
| 8,834,572 B2 | 9/2014 | Averous et al. |
| 8,840,623 B2 | 9/2014 | Reiley |
| 8,840,651 B2 | 9/2014 | Reiley |
| 8,858,601 B2 | 10/2014 | Reiley |
| 8,864,804 B2 | 10/2014 | Champagne et al. |
| 8,920,477 B2 | 12/2014 | Reiley |
| 8,986,348 B2 | 3/2015 | Reiley |
| 8,992,703 B2 | 3/2015 | O'Neill et al. |
| 8,998,999 B2 | 4/2015 | Lewis et al. |
| 9,011,504 B2 | 4/2015 | Reed |
| 9,039,743 B2 | 5/2015 | Reiley |
| 9,044,287 B2 | 6/2015 | Reed et al. |
| 9,056,014 B2 | 6/2015 | McCormick et al. |
| 9,072,562 B2 | 7/2015 | Weiner et al. |
| 9,072,564 B2 | 7/2015 | Reed et al. |
| 9,089,427 B2 | 7/2015 | Grohowski, Jr. |
| 9,089,431 B2 | 7/2015 | Grohowski, Jr. |
| D738,504 S | 9/2015 | Weiner et al. |
| 9,125,698 B2 | 9/2015 | Miller |
| 9,125,704 B2 | 9/2015 | Reed et al. |
| 9,135,374 B2 | 9/2015 | Jones et al. |
| 9,161,789 B2 | 10/2015 | Peyrot et al. |
| 9,168,074 B2 | 10/2015 | Prandi et al. |
| 9,180,010 B2 | 11/2015 | Dong et al. |
| 9,283,007 B2 | 3/2016 | Augoyard et al. |
| 9,403,213 B2 | 8/2016 | Lapszynski |
| 9,452,002 B2 | 9/2016 | Roman et al. |
| 9,492,215 B2 | 11/2016 | Augoyard et al. |
| 9,498,266 B2 | 11/2016 | McCormick et al. |
| 9,498,273 B2 | 11/2016 | Thoren et al. |
| 2001/0025199 A1 | 9/2001 | Rauscher |
| 2001/0049529 A1 | 12/2001 | Cachia et al. |
| 2002/0019636 A1 | 2/2002 | Ogilvie et al. |
| 2002/0055785 A1 | 5/2002 | Harris |
| 2002/0065561 A1 | 5/2002 | Ogilvie et al. |
| 2002/0068939 A1 | 6/2002 | Levy et al. |
| 2002/0082705 A1 | 6/2002 | Bouman et al. |
| 2002/0099395 A1 | 7/2002 | Acampora et al. |
| 2002/0133156 A1 | 9/2002 | Cole |
| 2002/0169066 A1 | 11/2002 | Cassidy et al. |
| 2002/0189622 A1 | 12/2002 | Cauthen et al. |
| 2003/0040805 A1 | 2/2003 | Minamikawa |
| 2003/0069645 A1 | 4/2003 | Ball et al. |
| 2003/0120277 A1 | 6/2003 | Berger |
| 2003/0130660 A1 | 7/2003 | Levy et al. |
| 2004/0002759 A1 | 1/2004 | Ferree |
| 2004/0093081 A1 | 5/2004 | Nilsson et al. |
| 2004/0102853 A1 | 5/2004 | Boumann et al. |
| 2004/0138756 A1 | 7/2004 | Reeder |
| 2004/0220574 A1 | 11/2004 | Pelo et al. |
| 2004/0220678 A1 | 11/2004 | Chow et al. |
| 2004/0230193 A1 | 11/2004 | Cheung et al. |
| 2005/0119757 A1 | 6/2005 | Hassler et al. |
| 2005/0124990 A1 | 6/2005 | Teague et al. |
| 2005/0251265 A1 | 11/2005 | Calandruccio et al. |
| 2005/0261768 A1 | 11/2005 | Trieu |
| 2005/0283159 A1 * | 12/2005 | Amara ............... A61B 17/7291 606/907 |
| 2006/0015181 A1 | 1/2006 | Elberg |
| 2006/0036322 A1 | 2/2006 | Reiley |
| 2006/0052725 A1 | 3/2006 | Santilli |
| 2006/0052878 A1 | 3/2006 | Schmieding |
| 2006/0074492 A1 | 4/2006 | Frey |
| 2006/0084998 A1 | 4/2006 | Levy et al. |
| 2006/0085075 A1 | 4/2006 | McLeer |
| 2006/0147332 A1 | 7/2006 | Jones et al. |
| 2006/0247787 A1 | 11/2006 | Rydell et al. |
| 2007/0038303 A1 | 2/2007 | Myerson et al. |
| 2007/0123993 A1 | 5/2007 | Hassler et al. |
| 2007/0142920 A1 | 6/2007 | Niemi |
| 2007/0156241 A1 | 7/2007 | Reiley et al. |
| 2007/0166122 A1 | 7/2007 | McDuff et al. |
| 2007/0185584 A1 | 8/2007 | Kaufmann et al. |
| 2007/0198088 A1 | 8/2007 | Biedermann et al. |
| 2007/0213831 A1 | 9/2007 | de Cubber |
| 2007/0239158 A1 | 10/2007 | Trieu et al. |
| 2008/0039949 A1 | 2/2008 | Meesenburg et al. |
| 2008/0132894 A1 | 6/2008 | Coilard-Lavirotte et al. |
| 2008/0154385 A1 | 6/2008 | Trail et al. |
| 2008/0177262 A1 | 7/2008 | Augoyard et al. |
| 2008/0195219 A1 | 8/2008 | Wiley et al. |
| 2008/0221697 A1 | 9/2008 | Graser |
| 2008/0221698 A1 | 9/2008 | Berger |
| 2008/0234763 A1 | 9/2008 | Patterson et al. |
| 2008/0269908 A1 | 10/2008 | Warburton |
| 2009/0005821 A1 | 1/2009 | Chirico et al. |
| 2009/0012564 A1 | 1/2009 | Chirico et al. |
| 2009/0018556 A1 | 1/2009 | Prandi |
| 2009/0138096 A1 | 5/2009 | Myerson et al. |
| 2009/0254189 A1 | 10/2009 | Scheker |
| 2009/0254190 A1 | 10/2009 | Gannoe et al. |
| 2010/0010637 A1 | 1/2010 | Pequignot |
| 2010/0016905 A1 | 1/2010 | Greenhalgh et al. |
| 2010/0016982 A1 | 1/2010 | Solomons |
| 2010/0057214 A1 | 3/2010 | Graham et al. |
| 2010/0121390 A1 | 5/2010 | Kleinman |
| 2010/0131014 A1 | 5/2010 | Peyrot |
| 2010/0131072 A1 | 5/2010 | Schulte |
| 2010/0161068 A1 | 6/2010 | Lindner et al. |
| 2010/0185295 A1 | 7/2010 | Emmanuel |
| 2010/0228301 A1 | 9/2010 | Greenhalgh et al. |
| 2010/0249942 A1 | 9/2010 | Goswami et al. |
| 2010/0256731 A1 | 10/2010 | Mangiardi |
| 2010/0256770 A1 | 10/2010 | Hakansson et al. |
| 2010/0262254 A1 | 10/2010 | Lawrence et al. |
| 2011/0004317 A1 | 1/2011 | Hacking et al. |
| 2011/0093084 A1 | 4/2011 | Morton |
| 2011/0093085 A1 | 4/2011 | Morton |
| 2011/0144644 A1 | 6/2011 | Prandi et al. |
| 2011/0208304 A1 | 8/2011 | Justin et al. |
| 2011/0301652 A1 | 12/2011 | Reed et al. |
| 2011/0301653 A1 | 12/2011 | Reed et al. |
| 2012/0029579 A1 | 2/2012 | Bottlang et al. |
| 2012/0065692 A1 | 3/2012 | Champagne et al. |
| 2012/0083791 A1 | 4/2012 | Cheney et al. |
| 2012/0089197 A1 | 4/2012 | Anderson |
| 2012/0197311 A1 * | 8/2012 | Kirschman ........ A61B 17/7098 606/104 |
| 2012/0259419 A1 | 10/2012 | Brown et al. |
| 2013/0053975 A1 | 2/2013 | Reed et al. |
| 2013/0060295 A1 | 3/2013 | Reed et al. |
| 2013/0066435 A1 | 3/2013 | Averous et al. |
| 2013/0123862 A1 | 5/2013 | Anderson et al. |
| 2013/0131822 A1 | 5/2013 | Lewis et al. |
| 2013/0150965 A1 | 6/2013 | Taylor et al. |

(56) References Cited

U.S. PATENT DOCUMENTS

| | | |
|---|---|---|
| 2013/0190761 A1 | 7/2013 | Prandi et al. |
| 2013/0190831 A1 | 7/2013 | Ek et al. |
| 2013/0231744 A1 | 9/2013 | Taylor et al. |
| 2013/0317559 A1 | 11/2013 | Leavitt et al. |
| 2013/0325077 A1 | 12/2013 | Champagne et al. |
| 2014/0005219 A1 | 1/2014 | Foster et al. |
| 2014/0039630 A1 | 2/2014 | Peyrot et al. |
| 2014/0058462 A1 | 2/2014 | Reed et al. |
| 2014/0107712 A1 | 4/2014 | Fallin et al. |
| 2014/0142715 A1 | 5/2014 | McCormick |
| 2014/0180428 A1 | 6/2014 | McCormick |
| 2014/0188239 A1 | 7/2014 | Cummings |
| 2014/0257509 A1 | 9/2014 | Dacosta et al. |
| 2014/0276827 A1 | 9/2014 | Roman et al. |
| 2014/0277554 A1 | 9/2014 | Roman et al. |
| 2014/0309747 A1 | 10/2014 | Taylor et al. |
| 2014/0316474 A1 | 10/2014 | Graham |
| 2014/0343615 A1 | 11/2014 | Cheney et al. |
| 2015/0011998 A1 | 1/2015 | McCormick et al. |
| 2015/0066097 A1 | 3/2015 | Biedermann |
| 2015/0073413 A1 | 3/2015 | Palmer et al. |
| 2015/0094778 A1 | 4/2015 | McCormick et al. |
| 2015/0112341 A1 | 4/2015 | Penzimer et al. |
| 2015/0112446 A1 | 4/2015 | Melamed et al. |
| 2015/0150607 A1 | 6/2015 | Chen et al. |
| 2015/0164563 A1 | 6/2015 | Lewis et al. |
| 2015/0223848 A1 | 8/2015 | McCormick |
| 2015/0223849 A1 | 8/2015 | McCormick et al. |
| 2015/0223850 A1 | 8/2015 | Reed |
| 2015/0223853 A1 | 8/2015 | Appenzeller et al. |
| 2015/0342655 A1 | 12/2015 | Reed et al. |
| 2016/0058484 A1* | 3/2016 | McCombs-Stearnes ............ A61B 17/7283 606/62 |
| 2016/0338751 A1 | 11/2016 | Kellar et al. |
| 2017/0065310 A1 | 3/2017 | Girod et al. |
| 2018/0161170 A1* | 6/2018 | Petranto ................ A61F 2/4225 |

FOREIGN PATENT DOCUMENTS

| | | |
|---|---|---|
| CA | 2836654 A1 | 6/2014 |
| CA | 2837497 A1 | 6/2014 |
| EP | 0042808 A1 | 12/1981 |
| EP | 0340159 A1 | 11/1989 |
| EP | 0420794 A1 | 4/1991 |
| EP | 0454645 A1 | 10/1991 |
| EP | 1300122 A2 | 4/2003 |
| EP | 1356794 A3 | 11/2003 |
| EP | 1582159 A1 | 10/2005 |
| EP | 1923012 A1 | 5/2008 |
| EP | 2228015 A3 | 3/2011 |
| EP | 2471477 A1 | 7/2012 |
| EP | 2471478 A1 | 7/2012 |
| EP | 2544633 A1 | 1/2013 |
| EP | 2749236 A3 | 10/2014 |
| FR | 2663838 A1 | 1/1992 |
| FR | 2725126 A1 | 4/1996 |
| FR | 2783702 A1 | 3/2000 |
| FR | 2787313 A1 | 6/2000 |
| FR | 2794019 A1 | 12/2000 |
| FR | 2801189 A1 | 5/2001 |
| FR | 2846545 A1 | 5/2004 |
| FR | 2856269 A1 | 12/2004 |
| FR | 2884406 | 10/2006 |
| FR | 2927529 A1 | 8/2009 |
| FR | 2935601 A1 | 3/2010 |
| FR | 2957244 A1 | 9/2011 |
| GB | 2119655 A | 11/1983 |
| GB | 2430625 B | 4/2007 |
| JP | S60145133 A | 7/1985 |
| JP | 03001854 A | 8/1991 |
| JP | H7303662 A | 11/1995 |
| JP | 2004535249 A | 11/2004 |
| JP | 3648687 B2 | 5/2005 |
| JP | 2007530194 A | 11/2007 |
| JP | 2008188411 A | 8/2008 |
| JP | 2008537696 A | 9/2008 |
| JP | 4695511 B2 | 6/2011 |
| JP | 5631597 B2 | 11/2014 |
| JP | 5645826 B2 | 12/2014 |
| KR | 20070004513 A | 1/2007 |
| KR | 20070022256 A | 2/2007 |
| KR | 101004561 B1 | 1/2011 |
| KR | 101235983 B1 | 2/2013 |
| WO | 9116014 A1 | 10/1991 |
| WO | 9625129 A1 | 8/1996 |
| WO | 9641596 A1 | 12/1996 |
| WO | 9726846 A1 | 7/1997 |
| WO | 9733537 A1 | 9/1997 |
| WO | 0117445 A1 | 3/2001 |
| WO | 03084416 A1 | 10/2003 |
| WO | 2005020830 A1 | 3/2005 |
| WO | 2005020831 A2 | 3/2005 |
| WO | 2005063149 A1 | 7/2005 |
| WO | 2005104961 A1 | 11/2005 |
| WO | 2006109004 A1 | 10/2006 |
| WO | 2007135322 A1 | 11/2007 |
| WO | 2008057404 A2 | 5/2008 |
| WO | 2008112308 A1 | 9/2008 |
| WO | 2008129214 A2 | 10/2008 |
| WO | 2009055952 A1 | 5/2009 |
| WO | 2009103085 A1 | 8/2009 |
| WO | 2010029246 A1 | 3/2010 |
| WO | 2011082343 A1 | 7/2011 |
| WO | 2011110784 A1 | 9/2011 |
| WO | 2011116078 A1 | 9/2011 |
| WO | 2011130229 A1 | 10/2011 |
| WO | 2012089330 A1 | 7/2012 |
| WO | 2012089331 A1 | 7/2012 |
| WO | 2013164819 A1 | 11/2013 |
| WO | 2014031947 A1 | 2/2014 |
| WO | 2014165123 A1 | 10/2014 |
| WO | 2015136212 A1 | 9/2015 |

OTHER PUBLICATIONS

HammerFix IP Fusion System, Hammertoe Deformity Surgical Technique, designed by Extremity Medical, published Mar. 31, 2014 (8 pages).

International Search Report for PCT/FR2008/050453 dated Nov. 4, 2008, 4 pages.

International Search Report, PCT/FR2006/050345, dated Aug. 30, 2006, 3 pages.

Intraosseous Fixation System, Hammertoe Surgical Technique, designed by OrthoHelix, published Aug. 23, 2012 (16 pages).

Japanese Office Action for Application No. 2011-526540 dated Aug. 13, 2013, 3 pages.

* cited by examiner

INTRAMEDULLARY IMPLANT AND METHOD OF USE

CROSS REFERENCE TO RELATED APPLICATIONS

This application is a continuation of U.S. application Ser. No. 16/587,793, filed on Sep. 30, 2019, which claims the benefit of U.S. application Ser. No. 15/612,733, filed on Jun. 2, 2017, now U.S. Pat. No. 10,470,807, which claims the benefit of the filing date of U.S. Provisional Patent Application No. 62/399,838, filed Sep. 26, 2016 and Provisional Patent Application No. 62/345,517, filed Jun. 3, 2016, the disclosures of which are hereby incorporated by reference herein as if fully set forth herein.

BACKGROUND OF THE INVENTION

The present disclosure relates generally to bone pins, and more particularly, to intramedullary implants which fix bones with respect to each other. In particular, the present disclosure relates to arthrodesis and osteosynthesis procedures in which bone portions, or two adjacent bones, are fused together.

An arthrodesis or osteosynthesis procedure is typically performed to improve stability and to place or maintain in compression two bone parts or bone fragments that should be consolidated. Stability is a critical factor for obtaining fusion of bone parts, while minimizing the attendant problems such as pain, swelling, etc. A compressive action on the bone portions serves to fuse the bones more rapidly in the position selected by the operator, such as the surgeon, during the operation.

Various technical solutions have been proposed for carrying out an arthrodesis, particularly in the foot, the hand, the wrist, etc. Historically, implants such as, for example, staples (with or without shape memory characteristics) and simple K-wires have been used, as have implants that may have shape memory or may otherwise be expandable. Certain of these implants can produce the compression beneficial to fusion of bone portions, but oftentimes can be difficult to implant. For instance, such implant can be difficult to manipulate in the surgical area, difficult to implant into bone, and/or difficult to orient properly in bone. As such, a need exists for an improved implant and instrumentation that provides the needed compression of the bones while also providing a simplified insertion technique.

BRIEF SUMMARY OF THE INVENTION

In one aspect of the present disclosure, a bone implant includes a proximal end, a distal end, a first portion extending between the proximal and distal ends having a maximum portion height and a minimum portion height, and a second portion extending between the proximal and distal ends having a maximum portion height and a minimum portion height. The second portion is connected to the first portion at the proximal end and the distal end and at least one of the first portion and the second portion is moveable relative to the other of the first portion and the second portion so as to transition the bone implant between a relaxed state wherein the first and second portions are separated by a first distance and a contracted state wherein the first and second portions are separated by a second distance different from the first distance. At least one of the proximal end and the distal end have the minimum portion height.

Additionally, the implant may also include an anchor element on at least one of the first portion and the second portion. The anchor element may be a plurality of barbs extending from at least one of the first and second portions. Of the plurality of barbs, a first set of barbs may be positioned adjacent the proximal end of the implant and extend from their respective first and second portions so that ends of the first set of barbs face a first direction, and a second set barbs may be positioned adjacent the distal end of the implant and extend from their respective first and second portions so that ends thereof face in a second direction opposite the first direction. Moreover, the first and second portions may taper outwardly from the proximal and distal ends so that a maximum width of the implant is positioned between the proximal and distal ends. The first and second portions may each include an engagement surface for engaging an instrument. The engagement surfaces of the first and second portions may be disposed at a location of the maximum width of the implant and between the first and second sets of barbs.

Continuing with this aspect, the first and second portions may be biased away from each other so that the bone implant is configured to be transitioned to or maintained in the contracted state via engagement with an instrument at a single contact point on each of the first portion and the second portion. The first and second portions may be bent along their length so that the proximal end is oblique to the distal end. Also, the implant may further include a first flange extending from the first portion towards the second portion and a second flange extending from the second portion towards the first portion. The first and second flange members may be spaced from one another when in the relaxed state and contact one another when in the contracted state. The first and second flanges may extend from inner surfaces of the first and second portions and may be located along a length of the first and second portions at a position of maximum width of the bone implant.

Furthermore, the proximal end may have a width greater than a width of the distal end. Also, the first and second portions may define a channel extending between the first and second portions and towards the proximal and distal ends. The channel may be adapted to accept a guide wire therein. The channel may be defined between inner surfaces of the first and second portions and upper surfaces of the proximal and distal ends.

In another aspect of the present disclosure, a bone implant includes a monolithic bone implant including first and second elongate portions and proximal and distal end portions. The first and second elongate portions each connect to the proximal and distal end portions so as to form a gap that is confined between the first and second elongate portions and proximal and distal end portions. The first and second elongate portions and proximal and distal end portions also define a channel that extends along a length of the implant from the distal end portion to the proximal end portion. The channel is configured to slidingly receive a guide wire.

Additionally, the gap may be defined by inner surfaces of the first and second elongate portions and inner surfaces of the proximal and distal end portions. The channel may be defined by inner surfaces of the first and second elongate portions and upper surfaces of the distal and proximal end portions.

In a further aspect of the present disclosure, a bone implant, includes a proximal end, a distal end, a first portion, a second portion connected to the first portion at the proximal and distal ends of the bone implant, a first flange extending from the first portion towards the second portion, and a second flange extending from the second portion towards the first portion. The first and second portions are biased away from each other and have a relaxed state where the first flange and second flange are separated by a first distance and a contracted state wherein the first flange and the second flange are separated by a second distance different from the first distance.

Additionally, the first and second portions may have a portion height, the proximal and distal ends of the implant may have an end height, and the first and second flanges may have a flange height smaller than the portion height. Also, the implant may include a channel defined between the first and second portions. The channel may have a height defined by the difference between the portion height and the flange height. Moreover, the implant may further include a channel defined between the first and second portions and within the portion height. Such channel may end above the end height at the proximal and/or distal end where the end height may be smaller than the portion height.

DETAILED DESCRIPTION

The implants, instructions and associated systems, kits, and methods, of the present disclosure are intended for use in tissue, in particular bone. While many of the exemplary methods disclosed herein are directed towards a use in a specific anatomy, such as the hand or foot, other uses, some of which are described herein, are also envisioned. As used herein, unless otherwise designated, "proximal" or "proximally" means closer to or towards an operator, e.g., surgeon, while "distal" or "distally" means further from or away from the operator. As used herein, the term "substantially" means to meet the criteria in such measure that one skilled in the art would understand that the benefit to be achieved, or the condition or property value desired, is met. As used herein, the term "about" shall be construed as a modifying term or value such that the amount so modified is not an absolute in order to take into account, at the very least, the degree of experimental error, technique error, instrument error, and the like commonly experienced in measuring values. Similarly, any ranges cited herein shall include the endpoints, including those that recite a range "between" two values.

The implants disclosed herein are generally intramedullary implants intended to aid in interphalangeal joint arthrodesis to correct anatomical issues, such as for example hammer-toe and other similar deformities, or to aid in osteosynthesis of two portions of a bone. In one exemplary use, this device may be utilized for arthrodesis of the bones of the toes or fingers, though its use in other anatomical locations is also envisioned. The general purpose of this type of implant, for example, is to hold two bones in place while fusion of the two bones occurs. As such, a portion of the device may be inserted in one of the bones (e.g., the proximal phalanx), and the remaining portion may be inserted into the other bone to be fused (e.g., the middle phalanx).

Figure 1:
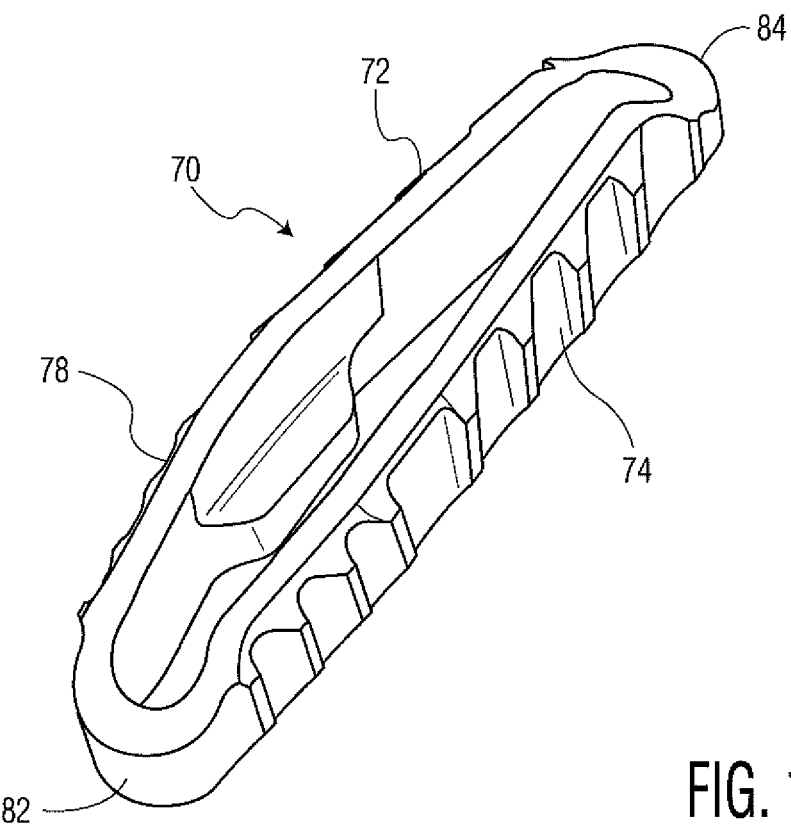
FIG. 1 is a perspective view of a bone implant in accordance with one embodiment of the present disclosure.
Figure 2:
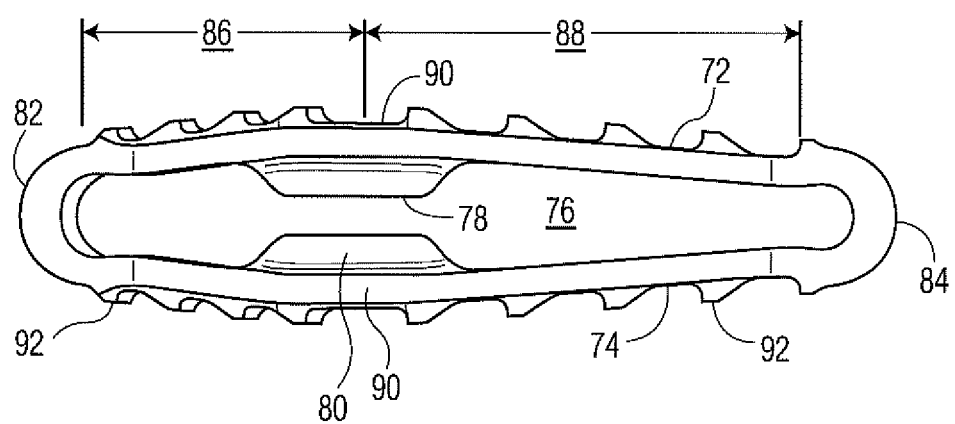
FIG. 2 is a top view of the bone implant of FIG. 1.
Figure 3:
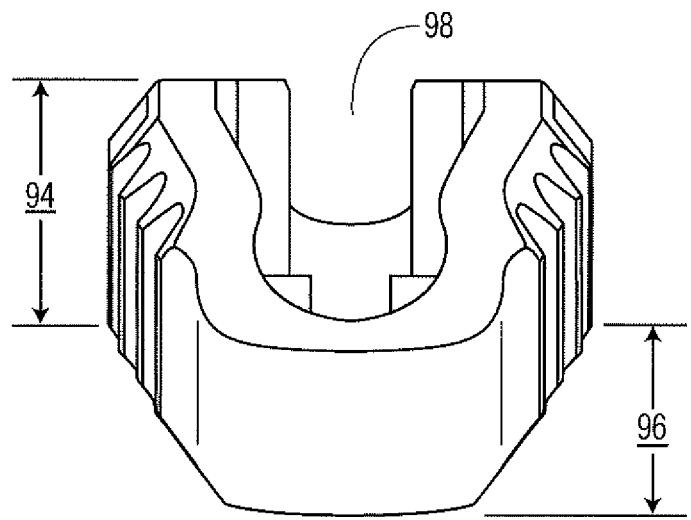
FIG. 3 is a front view of the bone implant of FIG. 1.

In one embodiment, FIGS. 1-4 illustrate a bone implant 70 having a first portion 72 and a second portion 74. The first and second elongate portions 72, 74 are separated by a space 76 when the implant 70 is in a relaxed state as best seen in FIG. 2. A first flange 78 extends from the first portion 72 and a second flange 80 extends from the second portion 74. When in the relaxed state as shown in FIG. 2, the flanges 78, 80 are separated from one another. As illustrated in FIG. 3, the first flange 78 may extend towards the second portion 74 and the second flange 80 may extend towards the first portion 72 such that the flanges can be opposite one another and facing one another. The first and second portions 72, 74 are connected at a proximal end 82 and a distal end 84 to form proximal and distal end portions or noses of implant 70, and is thus of monolithic construction, though the implant 70 could alternatively be separate and connectable portions. The first and second portions 72, 74 include a portion height 94 while the proximal and distal ends 82, 84 include an end height 96. Any of these heights can be different from any of the others, or alternatively they can all be of equal height to one another. As illustrated in FIGS. 2 and 3, for example, the portion height 94 is the same for both the first and second portion and is taller than the end height 96 at both the proximal and distal ends. Further, the end height 96 at both the proximal and distal end can be the same, or as illustrated, one may be taller than the other.

Figure 4:
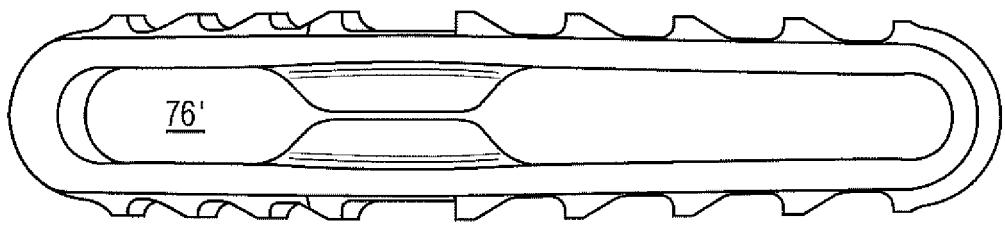
FIG. 4 is a top view of the bone implant of FIG. 1 in a compressed state.

The implant 70 is compressible such that it can transition between the relaxed state shown in FIG. 2 and a compressed state shown in FIG. 4. Preferably, the implant 70 has a "spring-like" characteristic such that the implant can be compressed through application of a force on the implant, but upon release of such force, the implant can "spring" back to its relaxed state. Such application of force may be performed by pressing the first and second portions 72, 74 towards one another using a surgeon's hand or a tool. To this end, the implant 70 may also have an engagement surface 90 on the first and second portions 72, 74. The engagement surface 90 can be positioned between a proximal portion 88 and a distal portion 86 of the implant 70, or anywhere else as desired. In particular, the engagement surfaces 90 may be positioned along the first and second portions 72, 74 where implant 70 is at its maximum width while said implant 70 is in a relaxed state, as best shown in FIG. 2. The engagement surface 90 can be shaped to be engaged by a tool, or alternatively provides a position for application of force by hand. Furthermore, the location of the engagement surface 90 allows a single tool, positioned at a single location of the first and second portions, to simultaneously transition the distal portion 86 and proximal portion 88 of the implant 70 between the relaxed state and the compressed state, though more than one tool may be used.

The first and second portions 72, 74 are separated by a reduced space 76' when the implant 70 is in the compressed state. The flanges 78, 80 are shown in FIG. 4 as adjacent to, but not in contact with, each other. Of course, the flanges could also contact one another when the implant is in the compressed state. The size of the flanges 78, 80 can be adjusted as desired to change the space between the first and second members 72, 74 when the implant 70 is in the compressed state. As such, smaller flanges may allow for additional compression of the portions 72, 74 while larger flanges may "bottom out" or contact one another which may prevent excessive compression. Further, the size of the space 76' can be adjusted to provide sufficient spacing for an insertion guide (e.g. K-wire) in a slot or channel 98 as shown in FIG. 3. The slot is formed by the proximal and distal ends 82, 84 as a bottom surface and the first and second portions 72, 74 (with a larger height) as side surfaces. The height of the portions 72, 74 allows the insertion guide to be positioned within the slot without extending beyond the perimeter established by the first and second portions. In other words, the slot 98 is defined by upper surfaces of the proximal and distal ends and inner surfaces of first and second portions 72, 74 as the first and second portions 72, 74 sit higher than proximal and distal ends. Moreover, the slot 98 allows the insertion guide to extend through the implant along a proximal to distal axis, and for the implant 70 to be able to travel along the insertion guide, without requiring an enclosed cannulation.

The implant 70 shown in FIGS. 1-4 can optionally include at least one anchoring element, illustrated here in the form of barbs 92. In this embodiment, the barbs 92 on the proximal portion 88 of the implant 70 face one direction while the barbs on the distal portion 86 face another direction. Orienting the barbs 92 in this way allows the distal portion 86 to be inserted into a first bone (e.g. middle or intermediate phalanx) and the proximal portion 88 to be inserted into a second bone (e.g. proximal phalanx), while preventing removal of the implant from either bone. Other barbs are also envisioned.

Implant 70, and indeed all embodiments herein, can be constructed of any material desired, such as metals, plastics, resorbable polymers, tissue such as bone, or the like. As to this embodiment, implant 70 can be constructed out of any material as it is the geometric design of the implant that provides for the spring-like recovery following compression. In other words, the design of implant 70 is such that the forces required to compress the implant are less than the yield stress of implant 70. To this end, the length, height, width and thickness of each portion can be adjusted as desired to obtain the desired spring characteristic, length of implant, width of implant, height of implant, etc.

Figure 5:
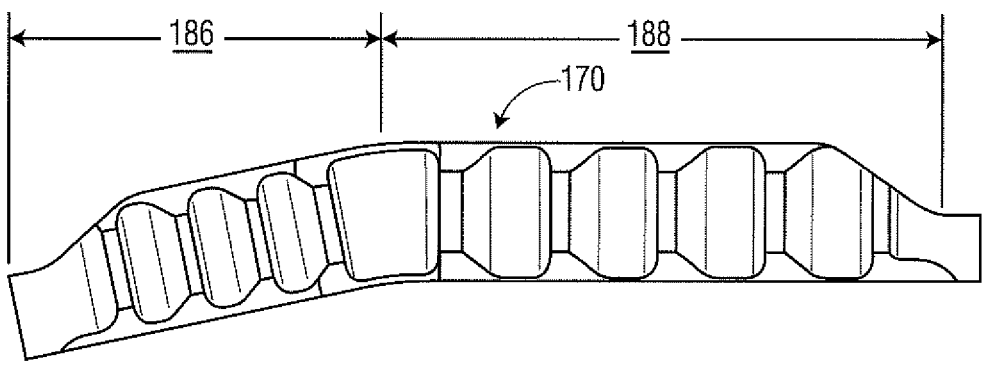
FIG. 5 is a side view of a bone implant in accordance with another embodiment of the present disclosure.
Figure 6:
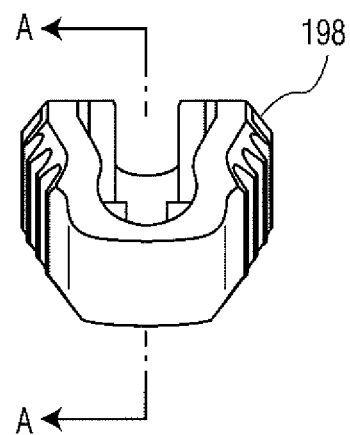
FIG. 6 is a front view of the bone implant of FIG. 5.
Figure 7:
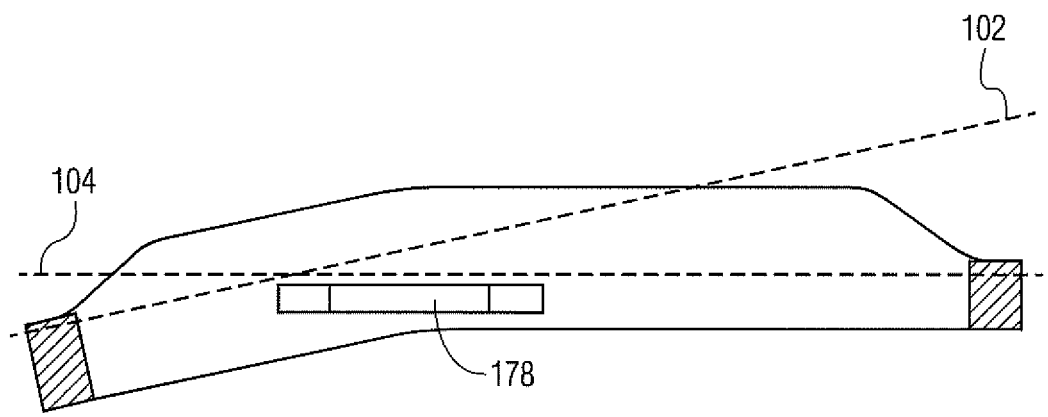
FIG. 7 is a sectional view along lines A-A of the bone implant of FIG. 6.

FIGS. 5-7 illustrate another embodiment of a bone implant having some of the features of the implant of FIGS. 1-4. However, implant 170 of FIGS. 5-7 includes a distal portion 186 which extends along a distal axis 102 and a proximal portion 188 which extends along a proximal axis 104. The proximal axis 104 is oblique to the distal axis 102. The offset axes allow the implant to approximate an anatomical positioning of the first and second bones with respect to each other. This angle may be any angle desired or useful for a particular anatomy.

FIG. 7 illustrates a sectional view of the implant 100 along line A-A of FIG. 6. The first and second flanges (labeled generally as "78") can be positioned anywhere desired on the implant 100, such as on the distal portion or on the proximal portion. Alternatively, the first flanges 178, as illustrated, can be partially positioned on the proximal portion 188 and partially on the distal portion 186. The slot 198 allows the implant 100, as discussed above, to ride along a straight insertion guide as the implant is inserted into bone such that a bent or curved guide is not required, though could be used. For example, the straight insertion guide could travel along the top surface of the proximal and distal ends (as described relative to FIGS. 1-4) and in between the first and second portions (as described relative to FIGS. 1-4). Further, the insertion guide may also contact one or both of the flanges, or alternatively, the flanges may remain separated from one another such that the insertion guide does not contact them (or, such that the insertion guide travels in between the flanges). In still a further alternative, the insertion guide could travel along the implant contacting one or both flanges and one of the proximal or distal ends. In yet a further alternative, the insertion guide could contact all three of the proximal and distal ends and the one or both flanges.

Figure 8:
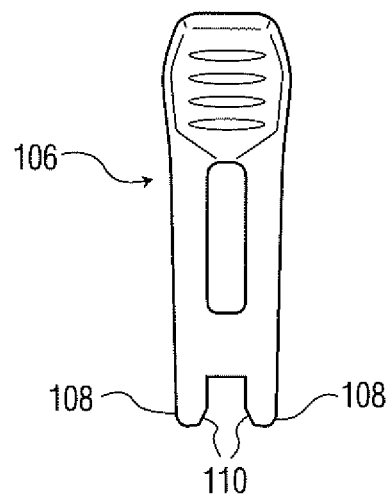
FIG. 8 is a front view of a clip in accordance with one embodiment of the present disclosure.
Figure 9:
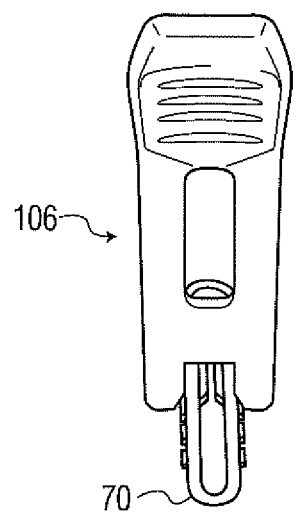
FIG. 9 is a perspective view of the clip of FIG. 8 coupled to the bone implant of FIG. 1.
Figure 10:
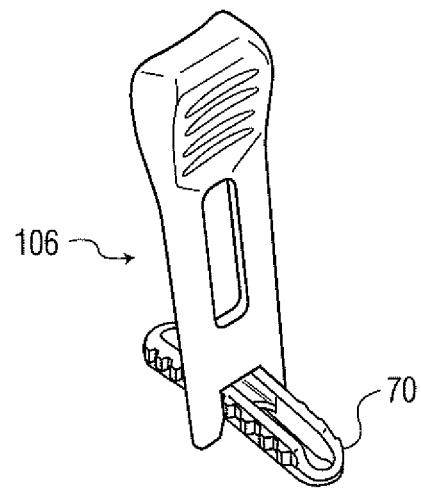
FIG. 10 is a perspective view of the clip of FIG. 8 coupled to the bone implant of FIG. 1.

FIGS. 8-10 illustrate one embodiment of a tool for use with the implants of the present disclosure. Namely, the tool is an inserter instrument or clip 106 which is used to transition or maintain the implant, such as implant 70 of FIGS. 1-4, in the compressed state. The clip 106 includes arms 108 which each have an angled portion 110. In use, for example with implant 70 of FIGS. 1-4, the engagement surface 90 of the implant 70 is positioned between the arms 108. The angled portions 110 can assist in transitioning the implant to the contracted state when the implant is pressed between the arms 108. In other words, as the engagement surface 90 is moved upwards into a position in between the arms 108, the taper of angled portions 110 may gradually compress the first and second portions 72, 74 towards one another from the implant's relaxed state (FIG. 2) to its compressed state (FIG. 4).

FIGS. 11A-11D shows one embodiment of a tool which may be used to handle and manipulate an implant of the present disclosure. As illustrated, an instrument/inserter handle 112 can be used to hold the implant, for example, implant 70, during an insertion or removal procedure. The handle 112 includes an opening 114 to receive either the proximal portion 82 or distal portion 84 of the implant 70. In addition, opening 114 can receive an insert, such as insert 200 shown in FIG. 11C. Insert 200 may be used to help secure implant 70 within handle 200. In this regard, insert 200 includes a body 202, flexible legs 204 extending from one end of the body 202, and flexible arms 206 extending from another end of body 202. Flexible legs 206 releasably connect to a post (not shown) within opening 114 to secure insert 200 to handle 112 and so that arms 206 are positioned adjacent the distal extent of opening 114. Flexible arms 206 are biased inward so as to pinch an implant 70 therebetween when such implant 70 is inserted into opening 114. The opening 114 is generally sized to receive the implant in the contracted state. Although the handle 112 is shown in FIGS. 11A-11D as receiving the straight implant 70, the handle can also receive the angled implant 100 of FIGS. 5-7, or any other implant described herein. In one exemplary use, the handle 112 may be used to compress the implant and position the implant onto the insertion guide previous disclosed. In some embodiments of handle 114, a cannulation may also extend through the handle 112 which may receive an insertion guide (e.g. K-wire). Such K-wire may be used in conjunction with implant 70, such as through channel 98.

Figure 12:
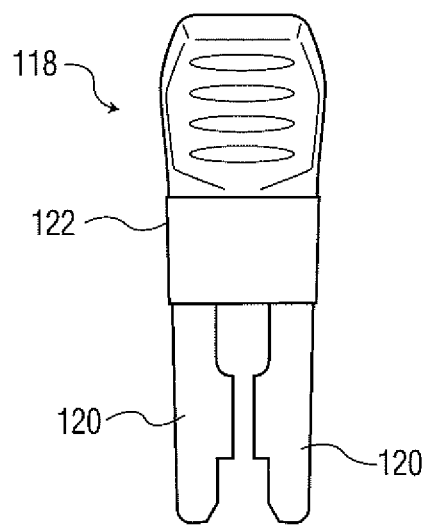
FIG. 12 is a front view of a clip in accordance with another embodiment of the present disclosure.
Figure 13:
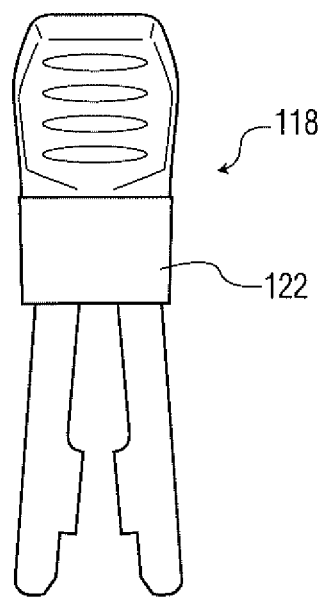
FIG. 13 is a front view of the clip of FIG. 12 in an expanded state.
Figure 14:
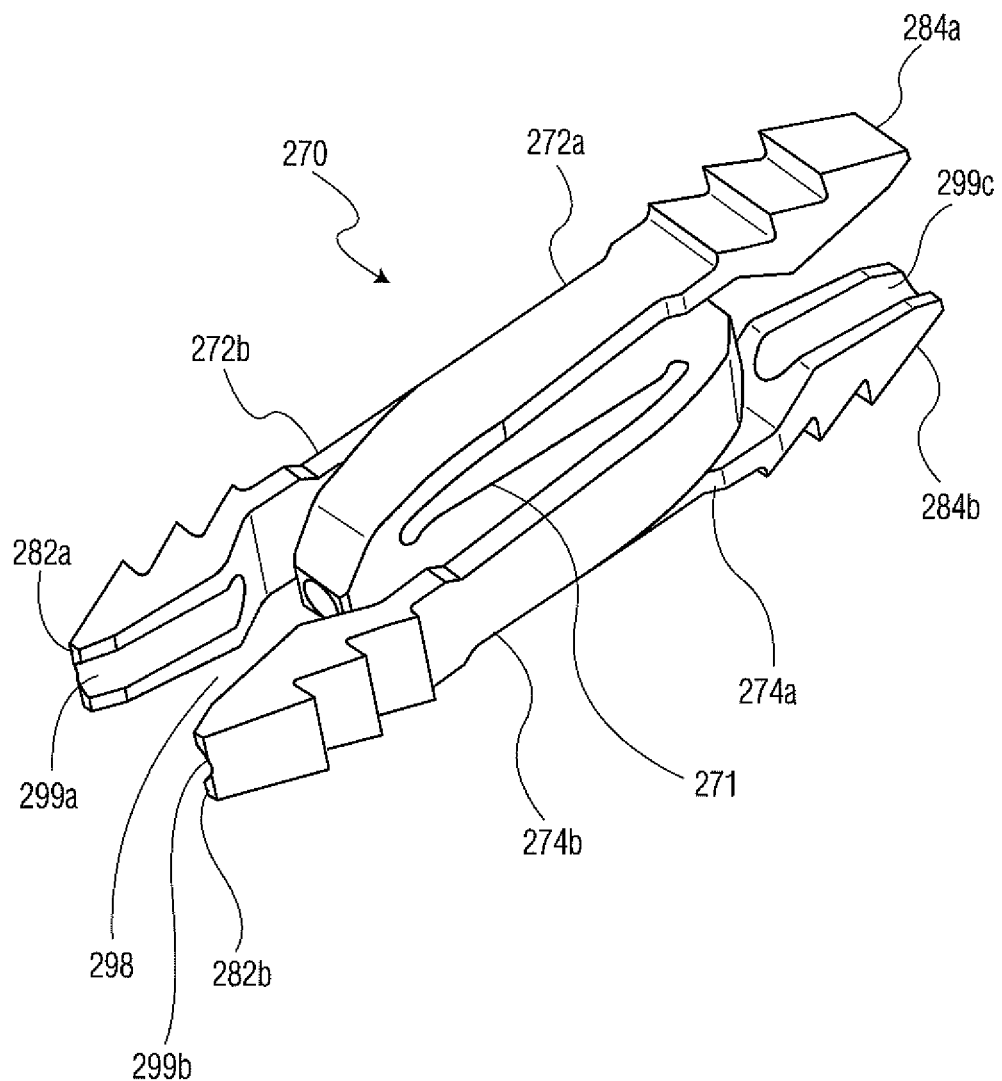
FIG. 14. is a perspective view of a bone implant in accordance with another embodiment of the present disclosure.
Figure 15:
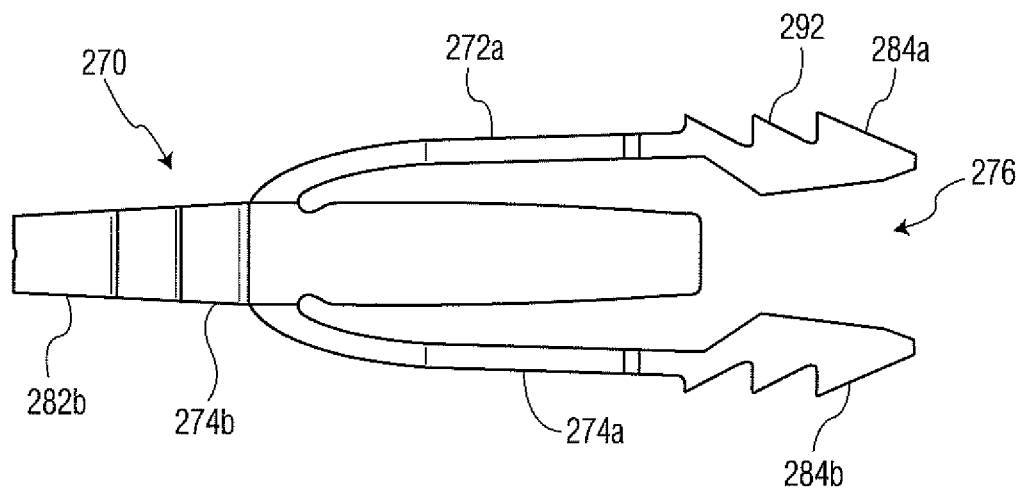
FIG. 15 is a top view of the bone implant of FIG. 14.
Figure 16:
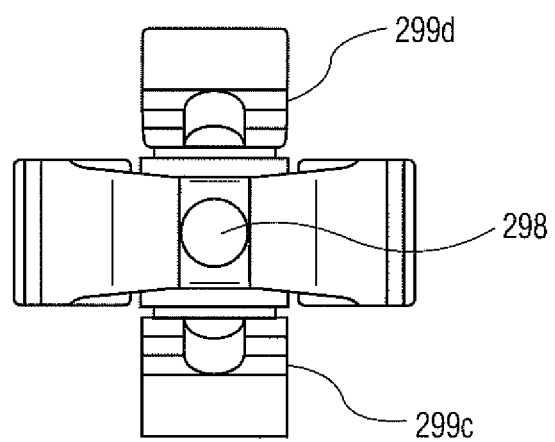
FIG. 16 is a front view of the bone implant of FIG. 14.
Figure 17:
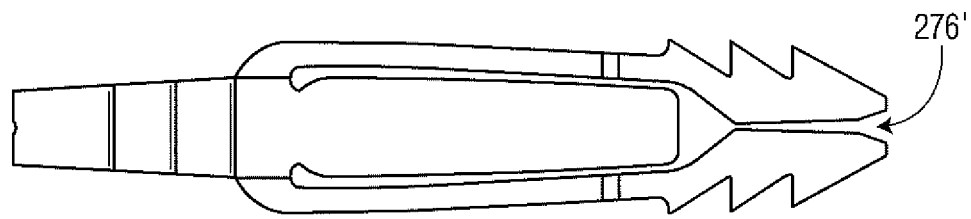
FIG. 17 is a top view of the bone implant of FIG. 14 in a compressed state.
Figure 18:
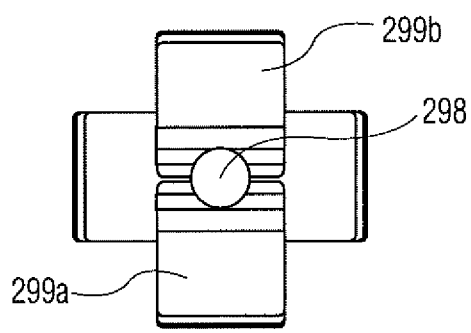
FIG. 18 is a front view of the bone implant of FIG. 14 in a compressed state.

FIGS. 12-13 illustrate another embodiment of a tool of the present disclosure, the tool being an inserter instrument or clip 118 with arms 120 that move between a closed configuration (FIG. 12) and an open configuration (FIG. 13). The clip 118 is similar to the clip of FIGS. 8-10 in that the clip 118 is designed to hold the implant during an implantation procedure in the compressed state. The clip 118 includes a sheath 122 which is moveable with respect to the arms 120. The arms 120 are in the closed configuration when the sheath 122 is in the advanced position (FIG. 12). The arms are in the open configuration when the sheath is in the retracted position (FIG. 13). An implant in the relaxed state can be positioned between the arms 120 in the open configuration. The sheath is then moved to the advanced position to transition the arms to the closed configuration. As the arms move toward each other they contact the engagement surface of the implant to transition the implant to the compressed state.

Figure 51A:
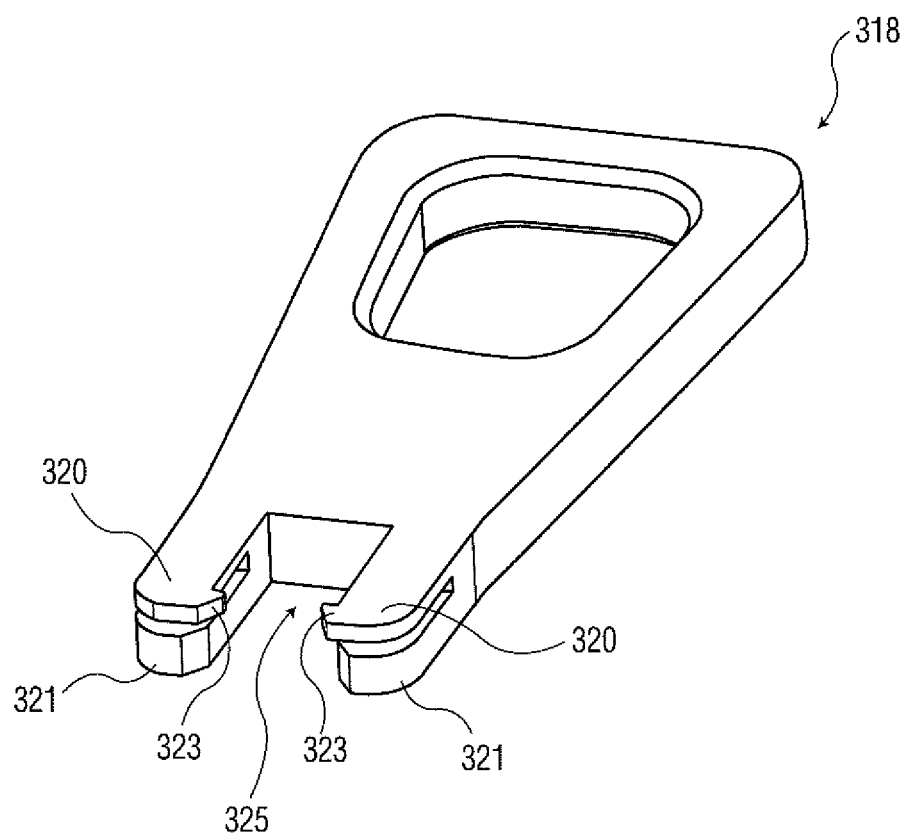
FIG. 51A is a perspective view of a clip in accordance with one embodiment of the present disclosure.
Figure 51B:
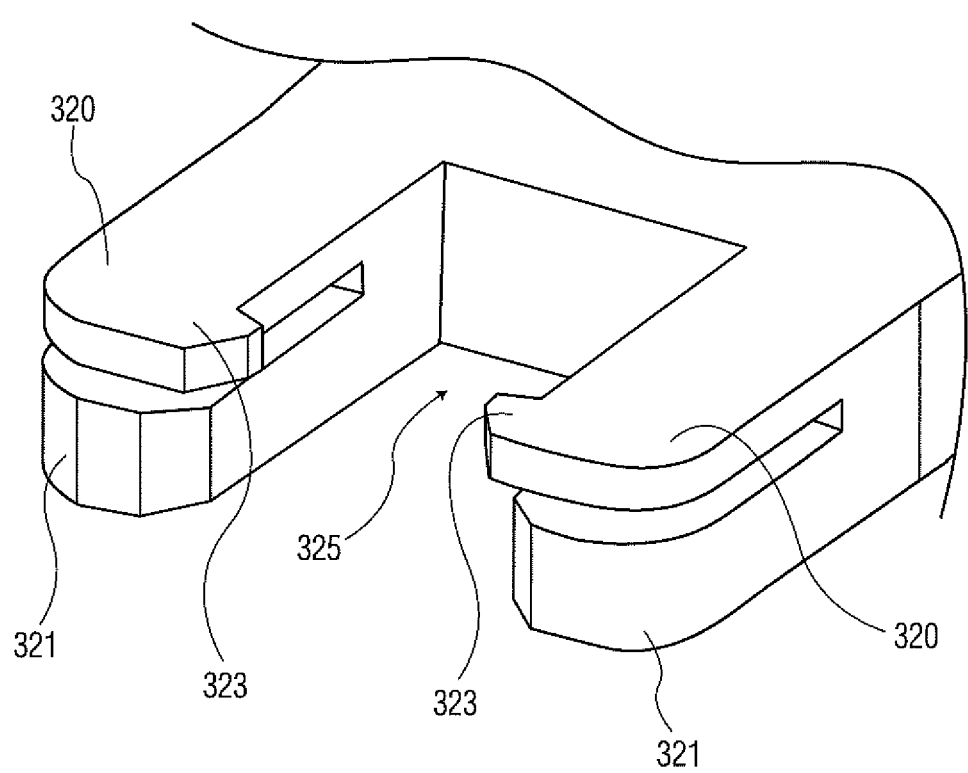
FIG. 51B is a focused perspective view of one end of the clip of FIG. 51A.

In yet another embodiment, FIGS. 51A-51B illustrate a tool, inserter instrument or clip 318, including an end having arms 320, 321 which together hold an implant within opening 325. Arms 321 may serve as additional width retention to minimize pivoting of the implant within the tool. Arms 320 include beveled tips 323 which hold the implant within opening 325. Specifically, arms 320 may have an amount of flexibility such that an implant may be positioned against the bevels of tips 323, and upon application of force on the tool 318 towards the implant, the tapered surfaces of the tips 323 force the arms 320 away from one another to allow passage of the implant into the opening 325. Once the implant moves past tips 323, the arms return to their original position to maintain the implant within opening 325. Similarly, upon implantation of the implant, removal of the tool 318 from the implant can be performed by pulling back on the tool whereby the shape of the tips 323 flex the arms away from one another such that the implant can slide past the tips.

Figure 52A:
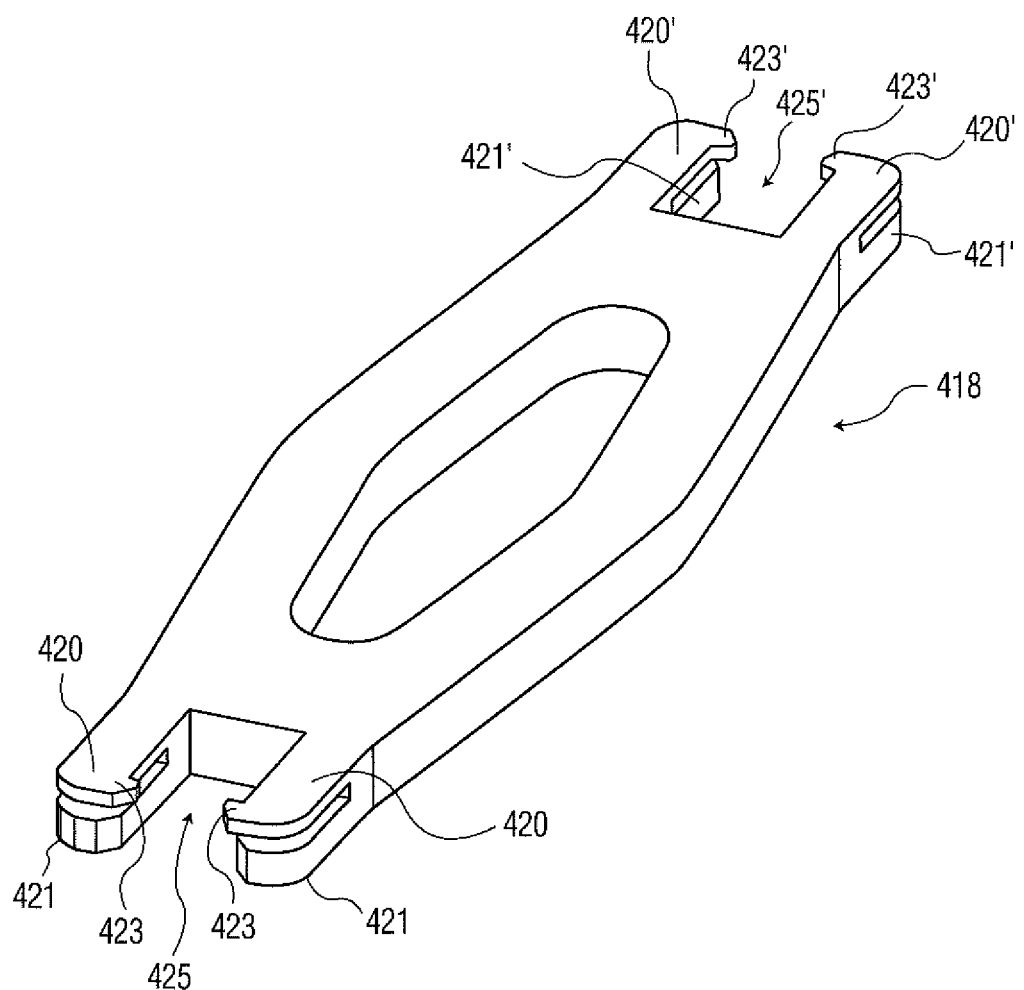
FIG. 52A is a perspective view of a clip in accordance with another embodiment of the present disclosure.
Figure 52B:
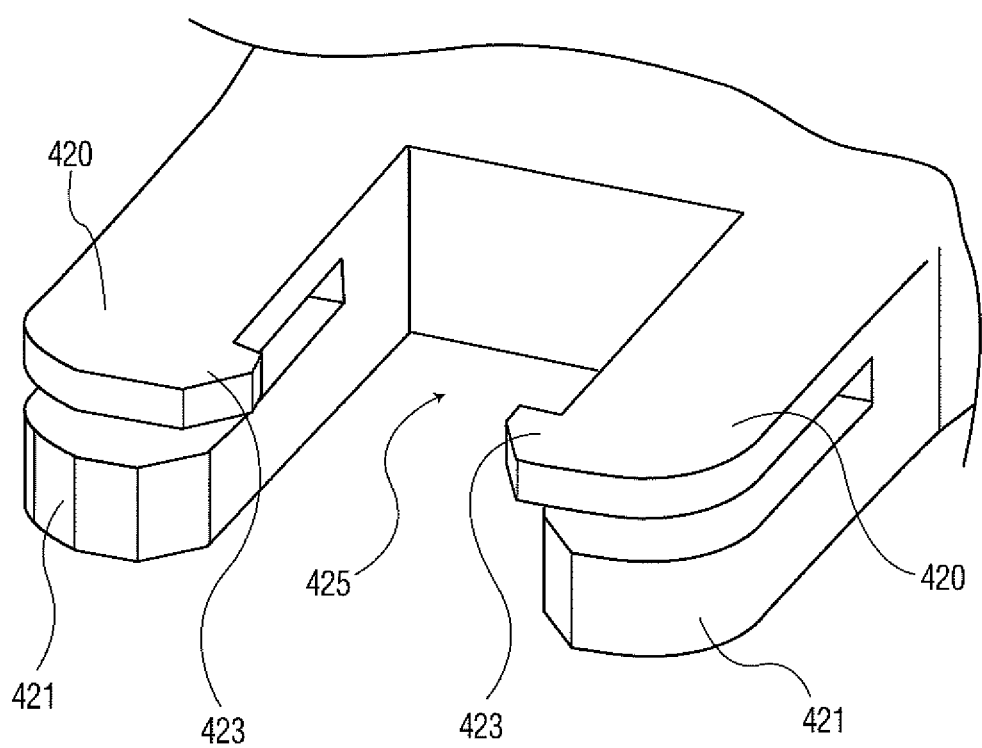
FIG. 52B is a focused perspective view of one end of the clip of FIG. 52A.

FIGS. 52A and 52B illustrate another embodiment of a tool 418. Tool 418 is similar to tool 318 (and as such like reference numbers denote like structures), above, except tool 418 includes a second end opposite a first end. As such, tool 418 includes two openings 425, 425' defined by arms 420, 421 and 420', 421', respectively. As illustrated, the two ends may be of different sizes to accommodate different sizes of implants. Alternatively, the two openings 425, 425' could have different shapes such that a single instrument could be used for insertion of differently shaped implants.

Figure 53A:
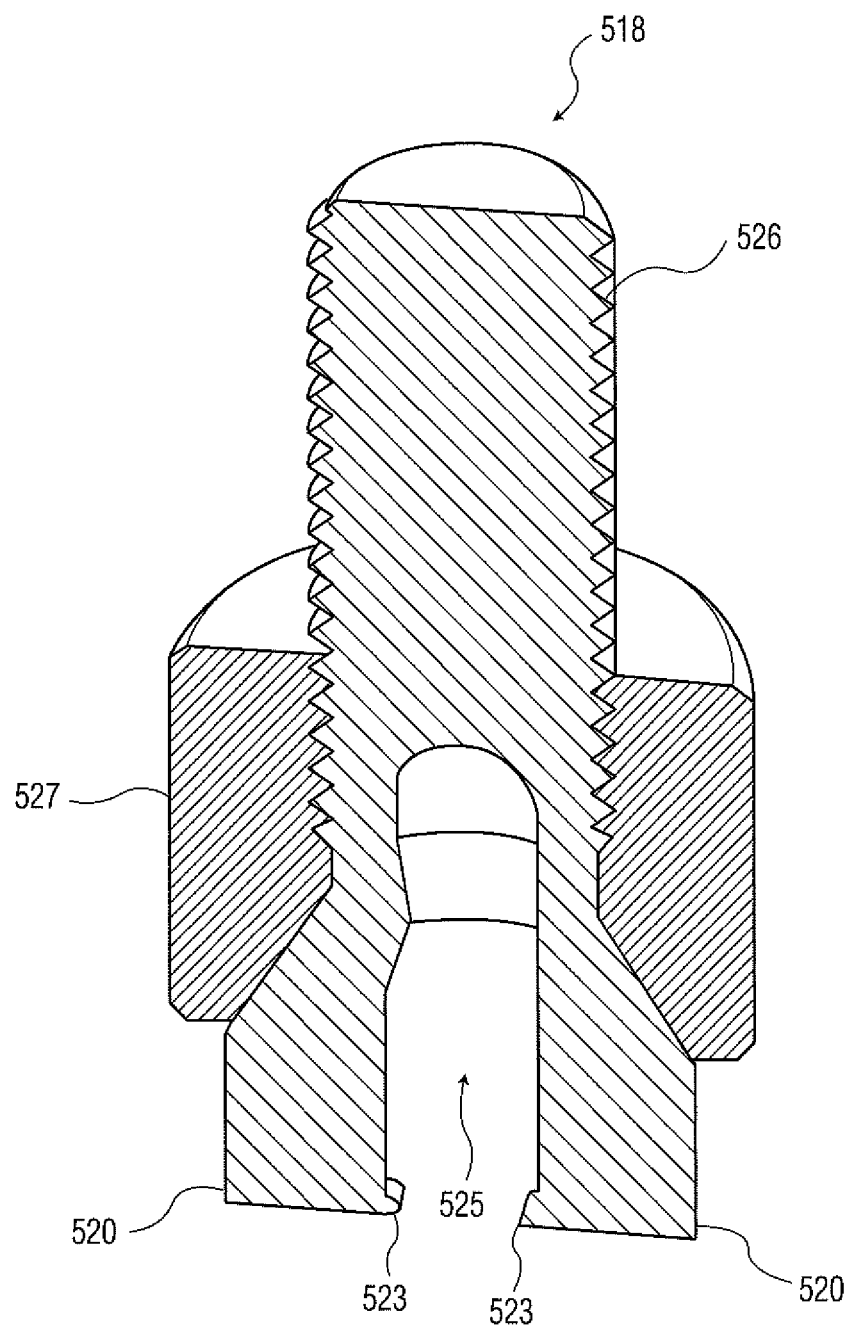
FIGS. 53A and 53B are cross-sectional views of the clip of FIG. 53C.
Figure 53B:
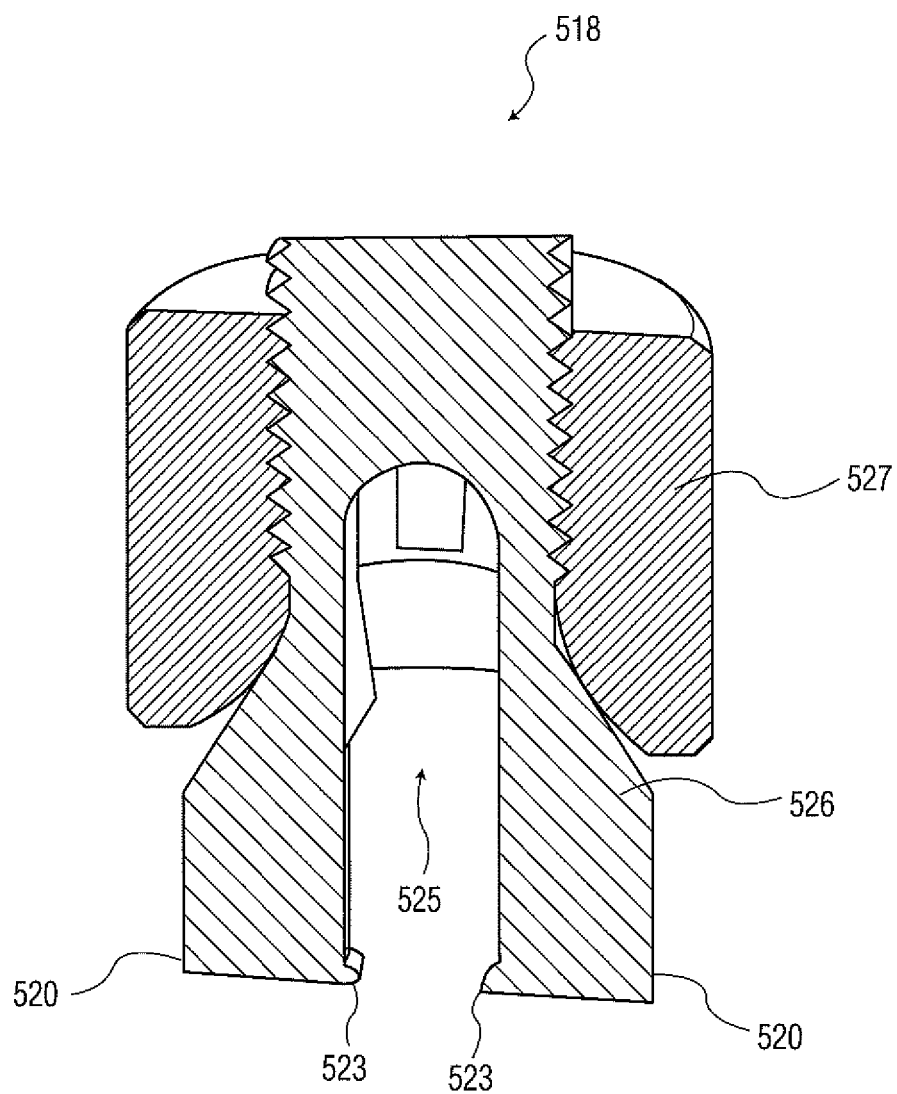
Figure 53C:
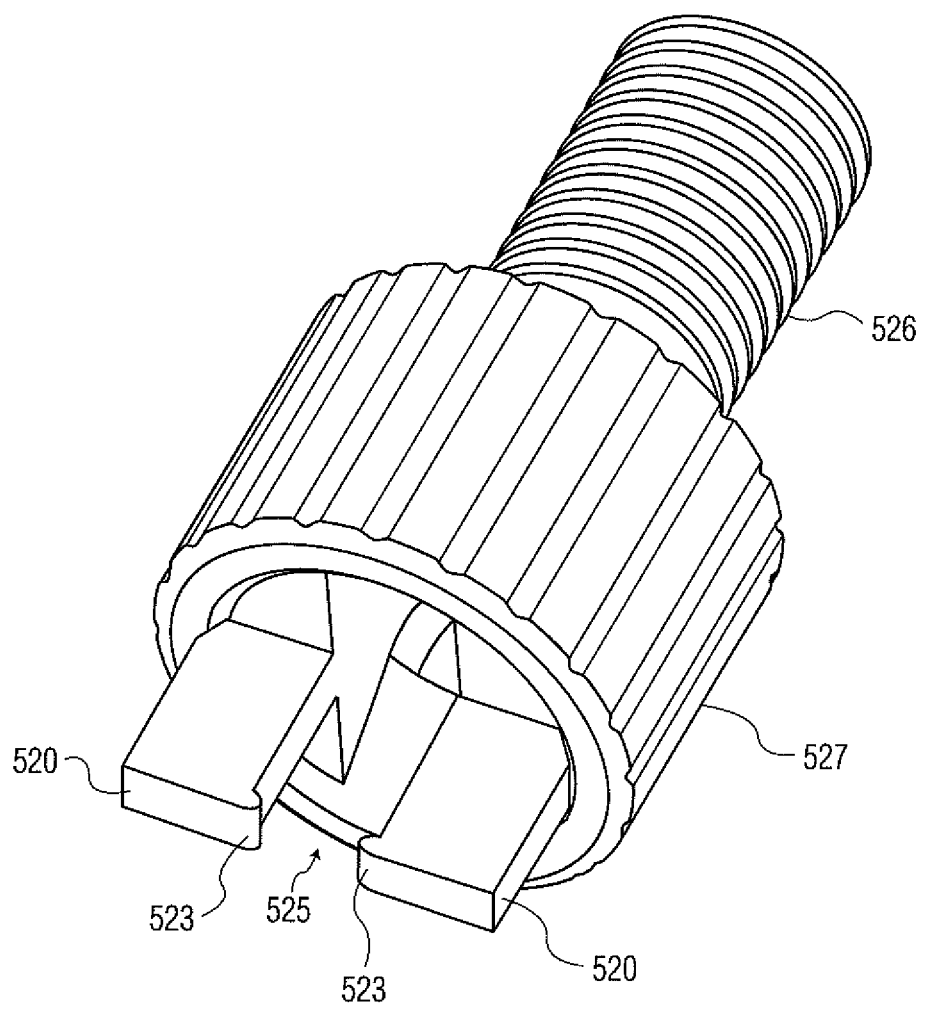
FIG. 53C is a perspective view of a clip in accordance with yet another embodiment of the present disclosure.

FIGS. 53A-C illustrates yet another embodiment of a tool 518. Tool 518 includes a base 526 having a body and arms 520 extending therefrom, and a collet 527 positioned on the body. As illustrated, the collet and base can have a threaded relationship but other engagement structures are also envisioned. As illustrated, the threaded collet can be rotated around the base in order to migrate along the length of the threaded body. The collet is intended to affect the distance of the arms 520 relative to one another. Specifically, the inner surface of the collet is tapered (illustrated as convex) which contacts a tapered surface of the base 526 on the arms 520. As the collet migrates downwards and the tapered surfaces contact one another, the arms are flexed inwards, and conversely, as the collet migrates upwards and the tapered surfaces move away from one another, the arms are allowed to return to their original, spread position. Thus, in use, an implant can be positioned within opening 525 and the collet can be migrated downwards such that the arms flex inwardly until the implant is contained within the opening 525 by arms 520 and tabs 523. Once the implant is implanted, and the tool 518 can be removed, the collet is migrated upwards, away from the arms 520, to allow the arms to return outwards to their original position to release the implant. Further, the adjustability of tool 518 may allow for the same tool to be used with variously sized and/or shaped implants.

The various tools and implants can be utilized to perform a surgical procedure on a patient in need thereof. In one embodiment, implant 70 may be implanted into two bones, for example, the proximal phalanx and the middle phalanx. While this method will be described using such specific implant, tools and anatomy, it is envisioned that any other implant and tools herein could be used in this method.

Generally speaking, in this method, the implant 70 is transitioned to its compressed state and inserted into the two bones. Once the implant is properly positioned, the force is removed and the implant returns towards or to its relaxed state, at which point the first and second portions 72, 74 abut the inner surface of the bone. The barbs 92, if present, provide additional securement against the bone surface such that the implant, and the two bones, are securely positioned relative one another. The ability of implant 70 to be compressed at a single location, engagement surface 90, leaves both ends 82, 84 of the implant exposed and ready for insertion.

Continuing with this exemplary method of a method of arthrodesis, the phalangeal bones are resected at the ends to be joined (i.e., the ends forming a joint for example, the head of the proximal phalanx and the base of the middle phalanx are both resected). A bore hole is then formed in each bone using a drill, broach, rasp or other such device known in the art.

The implant 70, in its compressed state, it brought into the surgical area. As discussed above, the implant can be compressed at a single location on the implant, which compresses both portions 86, 88. In this embodiment where arthrodesis is performed, the engagement surface 90 may be designed to be positioned at or near the joint line between the two prepared bones. This positioning may be beneficial as the tool, such as clip 106, can remain positioned on the implant until both portions 86, 88 are positioned in the first and second bones.

Continuing with this method, the implant ends 82, 84 are then moved into the first and second bones. While the implantation can be in any order, continuing with the example, the proximal portion 88 can first be positioned into the proximal phalanx until the prepared end of the proximal phalanx is adjacent to or abutting the tool, and then the distal portion 86 can be positioned into the middle phalanx until the prepared end of the middle phalanx is adjacent to or abutting the tool. In this position, the tool may then release the implant 70 and the tool is removed from the surgical area. Release of the implant allows the implant to return towards or to its relaxed state, thereby engaging the first and second bones. Any remaining gap between the bones, where the tool was previously positioned, can be reduced by manual compression of the bones.

Optionally, the above method may include the use of a guide, such as a K-wire and/or handle 112. In this embodiment, one end of the K-wire may be positioned in one of the first or second bone, while the implant 70 is positioned on the length of the K-wire such that the K-wire sits in slot 98. If handle 112 is used, the K-wire would then be positioned through slot 98 and into cannulation 116 of handle 112. The implant 70 would then be directed along K-wire and towards the bone, such that the K-wire guides the implant into the formed bore hole. These steps may be repeated for the other of the first and second bones, if desired.

Other tools are also envisioned for use with the implants and methods herein, including other instruments, bands (whether elastic or inelastic), or the like.

Though the implant is intended to remain permanently in the patient, there may be an unplanned and unintended need for removal (e.g., infection, irritation, etc.). The novel structure of the implants herein, such as implant 70, allows for ease of removal. For instance, in one embodiment, continuing with the above method for ease of illustration, the first and second bones can be separated slightly (as known in the art) to gain access to the implant. The tool, such as clip 106, is then re-engaged to the implant 70, preferably at the engagement surface (if exposed). This re-engagement compresses the implant to its compressed state such that the width of the implant is decreased on both portions 86, 88. The compression of the implant allows for ease of removal of the implant from both the first and second bones.

Also disclosed herein are various other embodiments of implants of the present disclosure. While other implant variations are envisioned, the following embodiments serve as further examples of implants that provide a single location for compression of the implant for insertion into a bone, portions of a bone, or adjacent bones. Similar features in the following embodiments as to the above embodiments of implant 70, 170 have similar functionality and use as detailed above. Further, these various implants of the present disclosure may be used in the exemplary methods provided above.

In one such embodiment, FIGS. 14-18 and 20 illustrate implant 270 which includes a central body 271 having a first end from which arms 272a, 274a extend and a second end from which arms 272b, 274b extend. As illustrated, the arms extend from the respective end of body 271 in a direction along the length of body 271 and outward away from the body. Further, arms 272a, 274a extend away in a similar direction along the length of body 271 but outward in opposite directions from one another, and similarly, arms 272b, 274b extend away in a similar direction along the length of body 271 but outward in opposite directions from one another. In other words, for example, arms 272a, 274a extend from a distal end of the body 271 to form a proximal end of implant 270, and arms 272b, 274b extend from a proximal end of the body 271 to form a distal end of implant 270. Each arm extends to a respective end 282a, 282b, 284a, 284b and one or more of the ends may include at least one barb 292 thereon. As above, the barbs may be shaped to allow for ease of insertion into a bone but resist the implant from pulling out of the bone.

Figure 20:
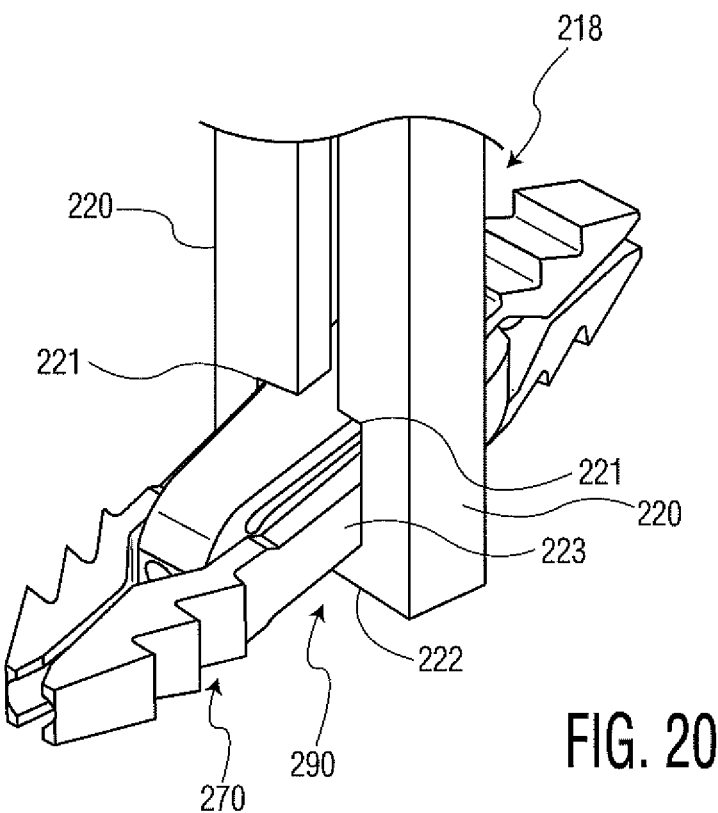
FIG. 20 is a perspective view of the bone implant of FIG. 14 positioned with one embodiment of a tool.
Figure 21:
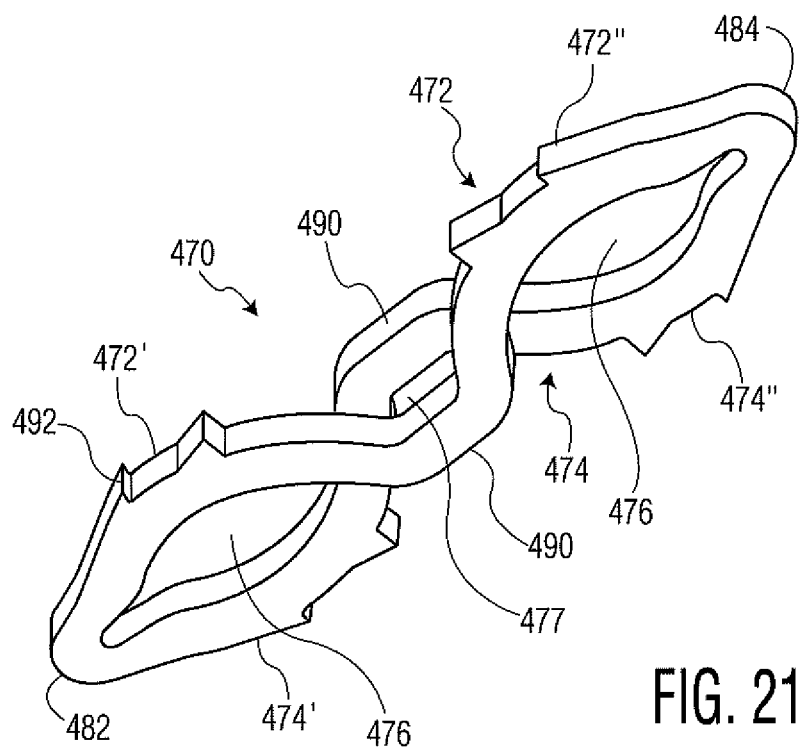
FIG. 21 is a perspective view of a bone implant in accordance with yet another embodiment of the present disclosure.
Figure 22:
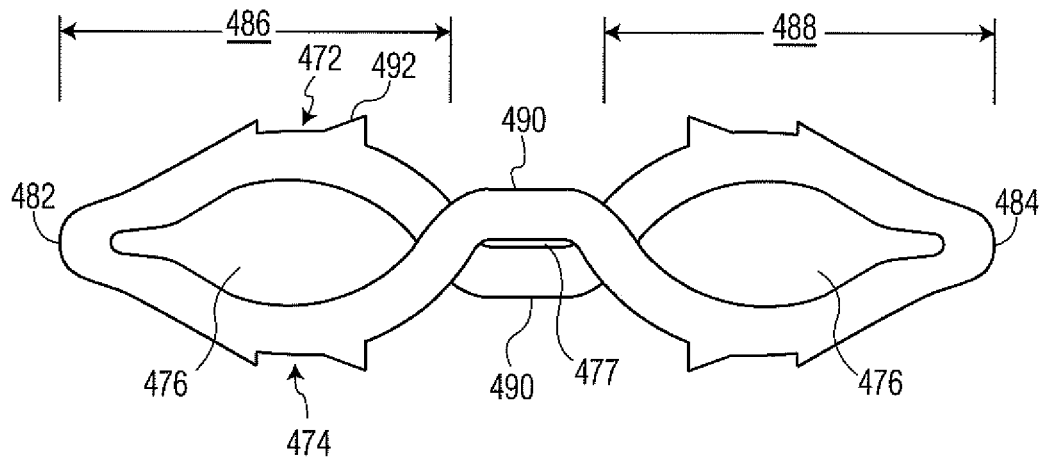
FIG. 22 is a side view of the bone implant of FIG. 21.
Figure 23:
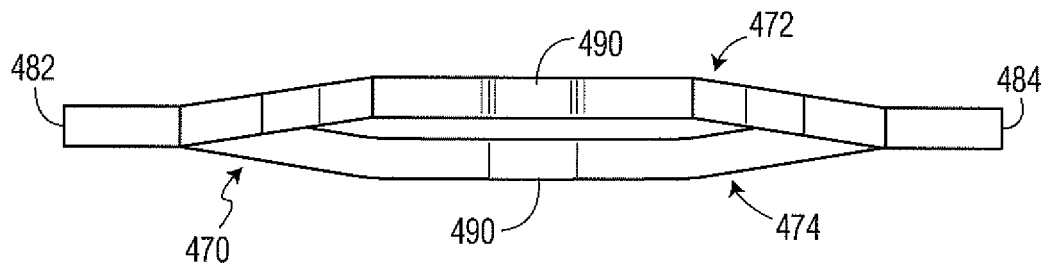
FIG. 23 is a top view of the bone implant of FIG. 21.

As particularly illustrated in FIGS. 15-18 and 20, implant 270 has a relaxed state (FIGS. 15 and 16) and a compressed state (FIGS. 17, 18 and 20) which, similar to as detailed above, includes a bias towards the relaxed state. Rather than the flanges 78, 80 found on implant 70, the arms of implant 270 will simply approach one another or even contact one another in the compressed state. A tool, such as clip 218 in FIG. 20 for example, can be used (or alternatively an operator's hand can be used) to transition the implant 270 from the relaxed state to the compressed state. Specifically, as in FIG. 20, clip 218 includes top, bottom and side surfaces 221, 222, 223 on arms 220 such that all four arms 272*a*, 274*a*, 272*b*, 274*b* can be transitioned to the compressed state simultaneously. Arms 272*a*, 274*a* are illustrated as being positioned on a plane substantially perpendicular to a plane on which arms 272*b*, 274*b* are similarly positioned, though other relative angles of each arm to the others are also envisioned. Similar to implant 70, implant 270 may also include a general engagement surface 290 on the four arms (as illustrated in FIG. 20) adjacent one another such that the clip 218 can engage the implant 270 at a single location along its length and compress all four arms. As such, implant 270 can be used in the method detailed above relative to implant 70.

As with the embodiments above, the thicknesses, lengths, materials, etc. of the implant can be designed as desired to provide the desired spring characteristic, length of implant, width of implant, height of implant, etc. Further, since implant 270 include individual arms, each independent arm relative to the others, may be designed differently as desired to provide the desired spring characteristic, length of arm, etc. of each individual arm.

Further, implant 270 can include slot 298 to allow passage of a guide, such as a K-wire, therethrough. Further each arm can include a concave surface 299*a*, 299*b*, 299*c*, 299*d* its the inner surface to allow passage of the K-wire when the arms are in the compressed position (see FIG. 18).

Figure 19:
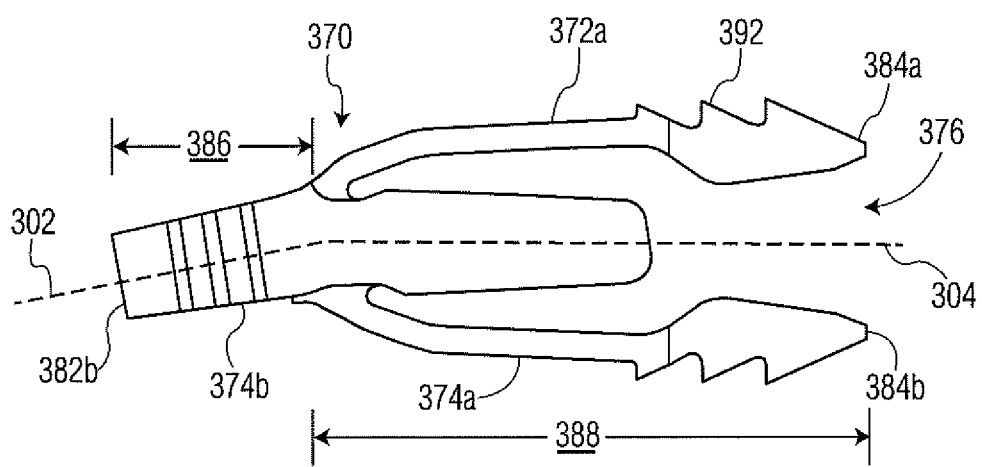
FIG. 19 is a side view of a bone implant in accordance with another embodiment of the present disclosure.

In another embodiment, FIG. 19 illustrates an implant 370 having some of the features of the implant of FIGS. 14-18 and 20. However, implant 370 of FIG. 19 (similar to implant 170 of FIGS. 5-7) includes a distal portion 386 which extends along a distal axis 302 and a proximal portion 388 which extends along a proximal axis 304. The proximal axis 304 is oblique to the distal axis 302 to approximate an anatomical positioning of first and second bones. This angle may be any angle desired or useful for a particular anatomy. As illustrated, the angle is formed along the length of arms 372*b* (behind arm 374*b*), 374*b*, and potentially through body 371 (behind arm 374*b*) though the location of the angle may be formed elsewhere along the length of the implant 370 as desired.

Figure 24:
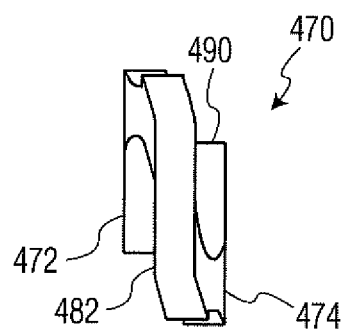
FIG. 24 is a front view of the bone implant of FIG. 21.

In another embodiment, illustrated in FIGS. 21-27, implant 470 has a first portion 472 and a second portion 474 connected to each other at a proximal end 482 and a distal end 484. Each of the first portion and second portion includes end sections 472', 472", 474', 474", and a middle section which, as illustrated, forces an engagement surface 490. End section 472' curves away from end section 474' from proximal end 482, and end section 472" curves away from 474" from distal end 484. Similarly, the respective end sections curve back towards one another, and past each other, towards engagement surface 490. These curves along first and second portions 472, 474 form two spaces 476 and a third space 477. However, in an alternative embodiment, the first and second portions might not cross past one another, and thus third space 477 may not be present as illustrated. Additionally, at least one part of the implant can include at least one barb 492. Either way, as shown in FIG. 24, the first and second portions are offset laterally relative to one another to provide an allowance for the movement of and/or interaction with engagement surfaces 490.

Figure 25A:
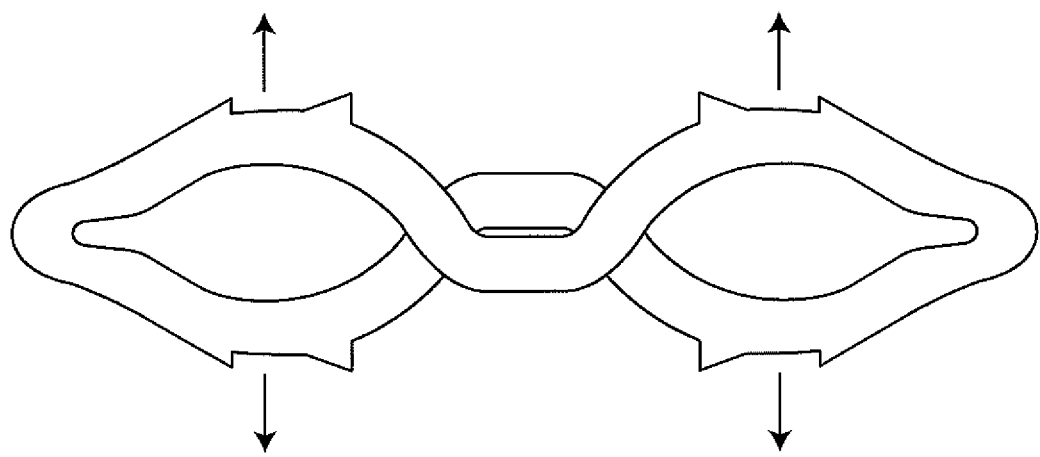
FIGS. 25A and 25B illustrate the transition from a relaxed state (FIG. 25A) to a compressed state (FIG. 25B).
Figure 25B:
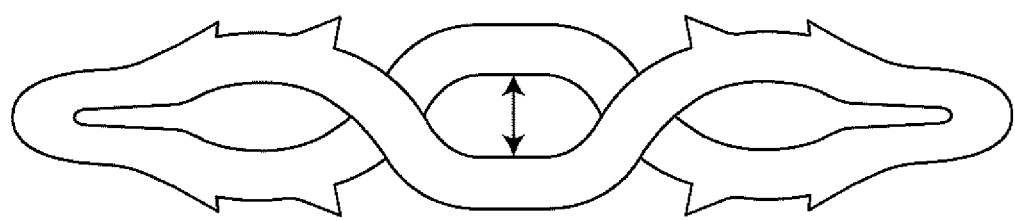
Figure 26:
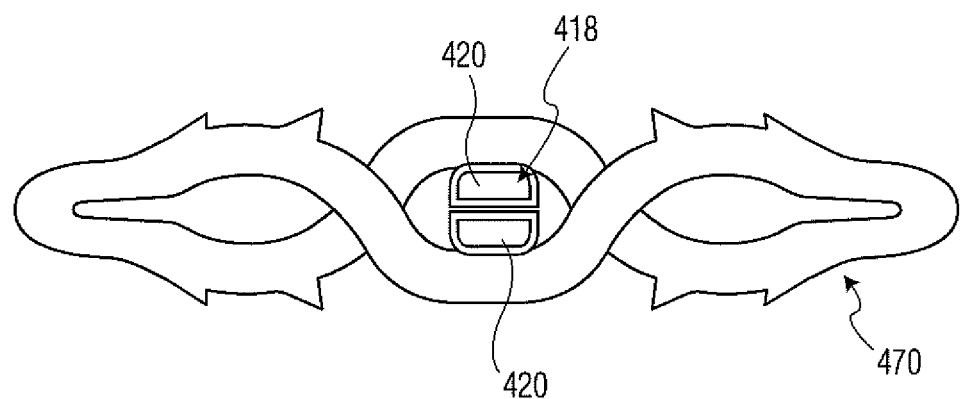
FIG. 26 is a side view of the bone implant of FIG. 21 positioned with one embodiment of a tool.

Similar to the other embodiments above, implant 470 includes a relaxed state, as in FIGS. 21-25A, and a compressed state, as in FIGS. 25B and 26. As such, a tool, such as clip 418 in FIG. 26, can be positioned at a single location along the length of the implant, i.e., engagement surface 490, and used to transition the implant to the compressed state. As shown, clip 418 includes arms 420 that can be positioned on the engagement surfaces 490, within space 476, and separated from one another to move engagement surfaces 490 away from one another. In turn, as in FIGS. 25A and 25B, as engagement surfaces 490 separate, end sections 472', 472" and 474', 474" move towards one another to compress the width of portions 486, 488 of the implant.

Figure 27:
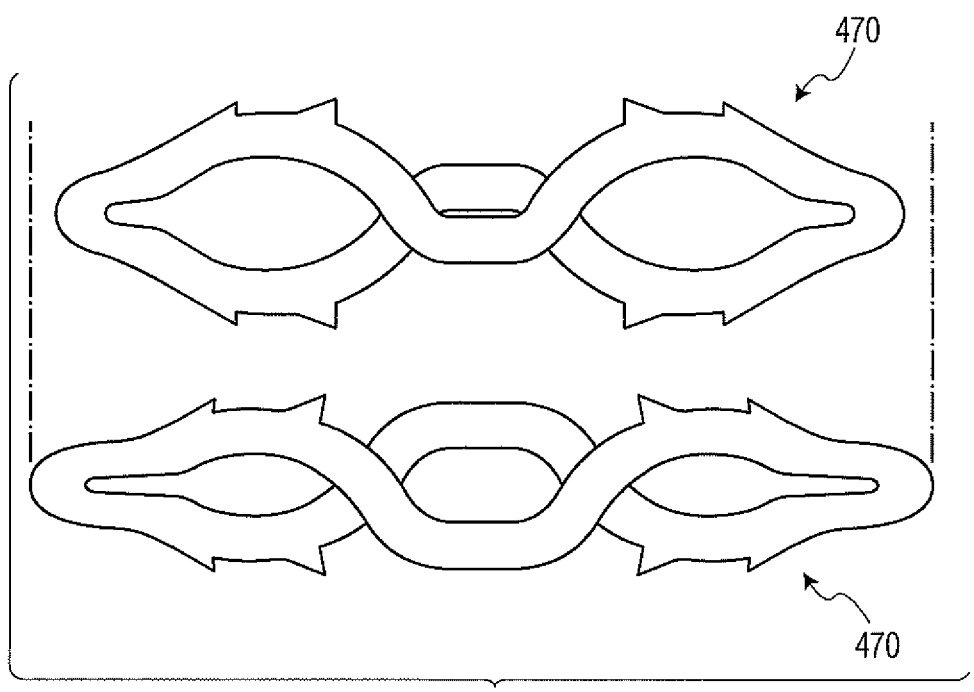
FIG. 27 illustrates the difference in length between the relaxed state and compressed state of the bone implant of FIG. 21.
Figure 28:
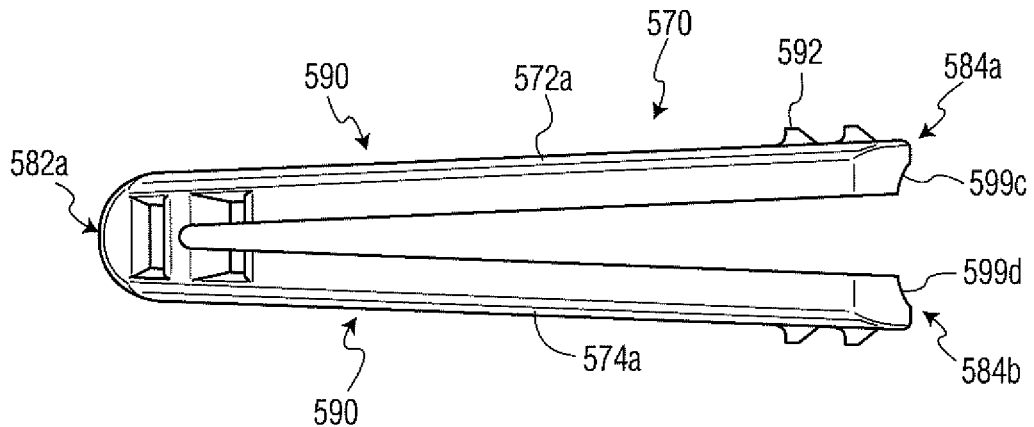
FIG. 28 is a top view of a bone implant in accordance with still another embodiment of the present disclosure.
Figure 29:
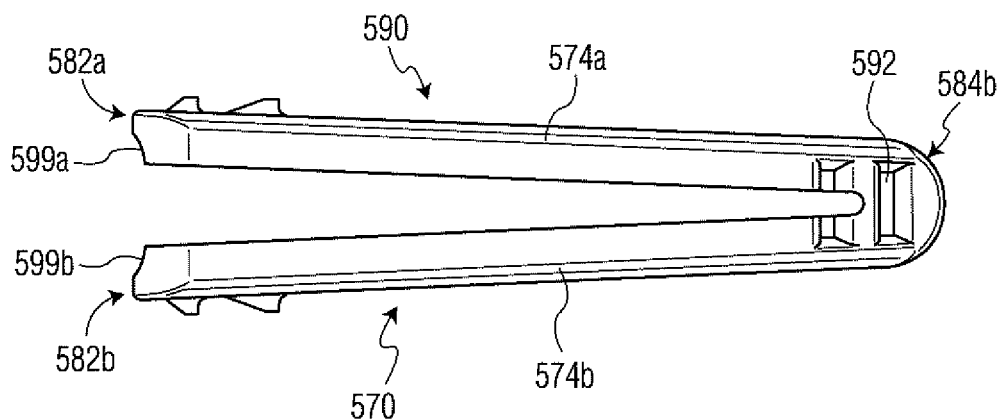
FIG. 29 is a side view of the bone implant of FIG. 28.
Figure 30:
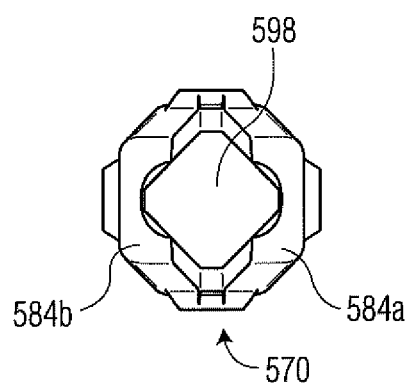
FIG. 30 is a front view of the bone implant of FIG. 28.
Figure 31:
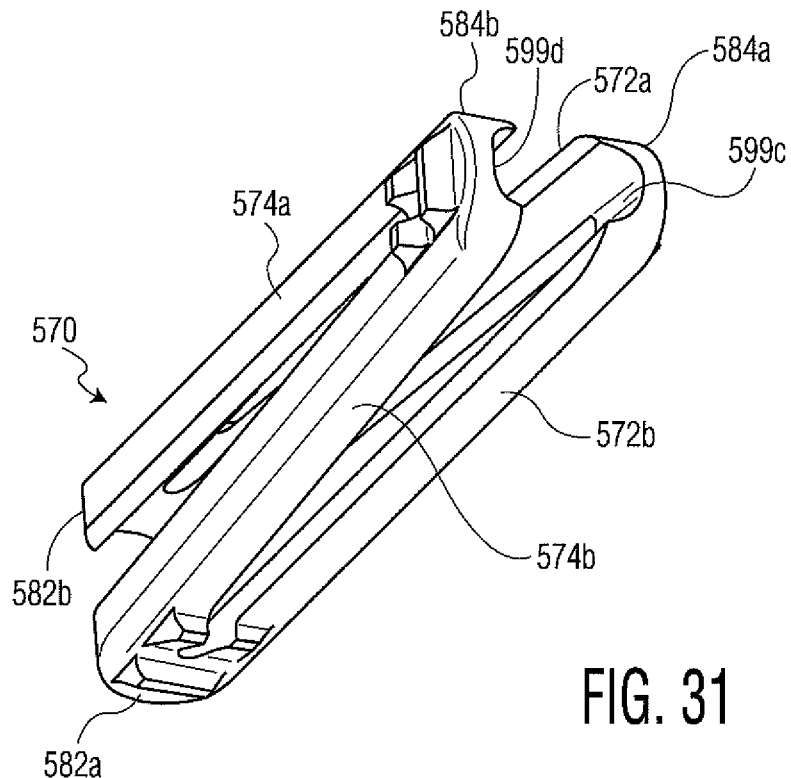
FIG. 31 is a perspective view of the bone implant of FIG. 28.

In this embodiment, as illustrated in FIG. 27, transitioning the implant from the relaxed state to the compressed state also may cause the implant to increase in length. Such elongation of implant 470 provides for a compression action on the bone portions in which it is implanted (one method of which is discussed in detail above). In other words, with the implant positioned in the bones in the compressed state, release of the tool allows the implant to return to the relaxed state. As this transition occurs, the implant engages the bones and pulls the bones towards one another as the length of the implant decreases. Thus, the aforementioned manual reduction of the bones may not be necessary in this example.

In another embodiment, the implant 470 could be angled (not shown), in similar fashion to implants 170, 370 discussed above.

In still another embodiment, illustrated in FIGS. 28-34, implant 570 includes four arms 572*a*, 572*b*, 574*a*, 574*b* that are sequentially connected to one another such that arm 572*a* connects with arm 572*b* at distal end 584*a*; arm 572*a* connects with arm 574*a* at proximal end 582*a*; arm 574*a* connects with arm 574*b* at distal end 584*b*; and arm 574*b* connects with arm 572*b* at proximal end 582*b*. As in implant 270, discussed above, proximal ends 582*a*, 582*b* are spaced apart from one another in a relaxed state and distal ends 584*a*, 584*b* are spaced apart from one another in the relaxed state, as illustrated in FIGS. 28-31. One or more of the proximal and/or distal ends can include at least one barb 292 thereon.

Figure 32:
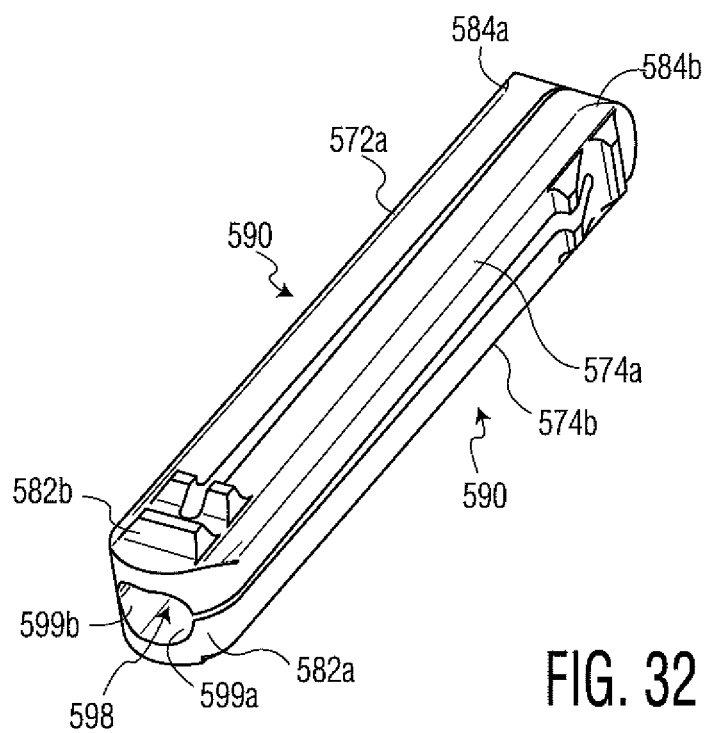
FIG. 32 is a perspective view of the bone implant of FIG. 28 in a compressed state.
Figure 33:
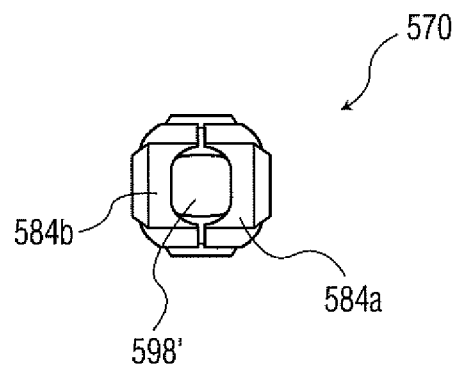
FIG. 33 is a front view of the bone implant of FIG. 28 in a compressed state.
Figure 34:
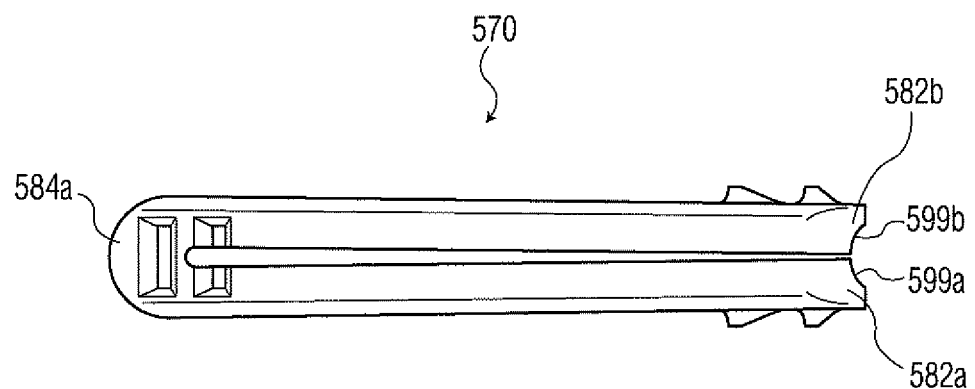
FIG. 34 is a side view of the bone implant of FIG. 28 in a compressed state.

FIGS. 32-34 illustrate a compressed state of implant 570 in which proximal ends 582*a*, 582*b* are brought towards one another, and may contact one another, and distal ends 584*a*, 584*b* are brought towards one another, and may contact one another. Alternatively, while the proximal and distal ends are illustrated as being generally parallel to one another at each end (i.e., end 582*a* relative to end 582*b*), and the opposing ends as being generally perpendicular to one another (i.e., end 582*a* relative to end 584*a*), these angles and relationships may be varied as desired.

As in the other embodiments, transition of the implant from the relaxed state to the compressed state can occur by application of a force to a single location along the length of the implant. As illustrated, a tool (not shown) can contact engagement surface 590, on at least one of the arms, and preferably on all four arms 572*a*, 572*b*, 574*a*, 574*b*, to apply such force to draw the arms towards one another. Again, similar to implant 270, slot 598 constricts to slot 598' upon transition to the compressed state, and arms include concave surfaces 599*a*, 599*b*, 599*c*, 599*d* to allow for passage of a guide, such as a K-wire, through the slot which may assist in insertion of the implant into the bone or bones.

Figure 35A:
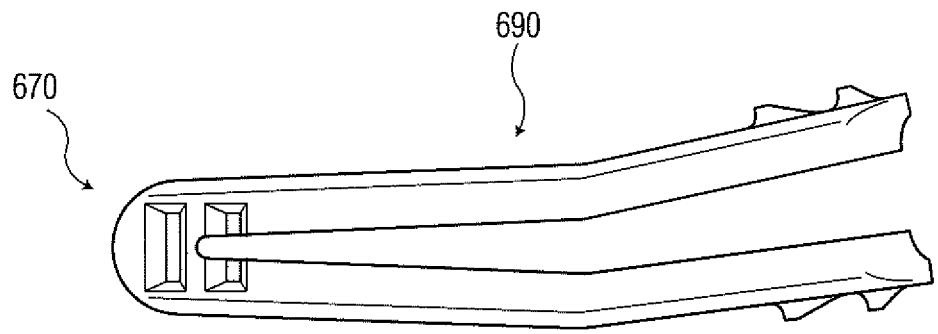
FIGS. 35A and 35B are side and top views of yet a further embodiment of the present disclosure.
Figure 35B:
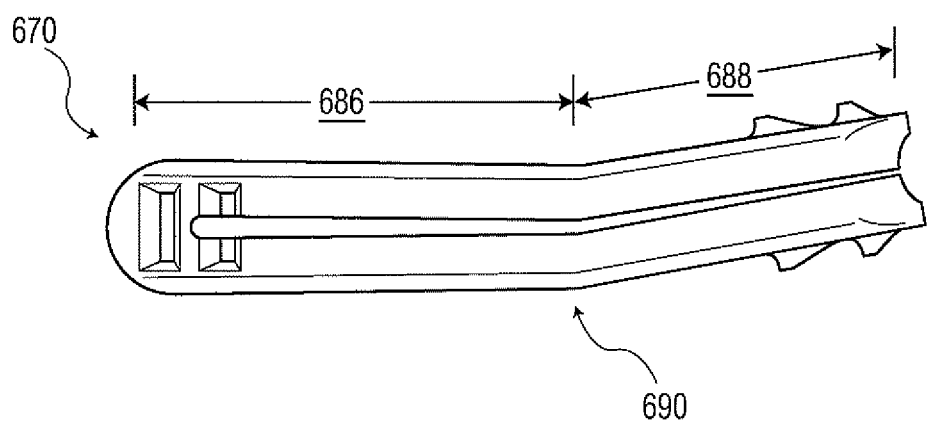
Figure 36:
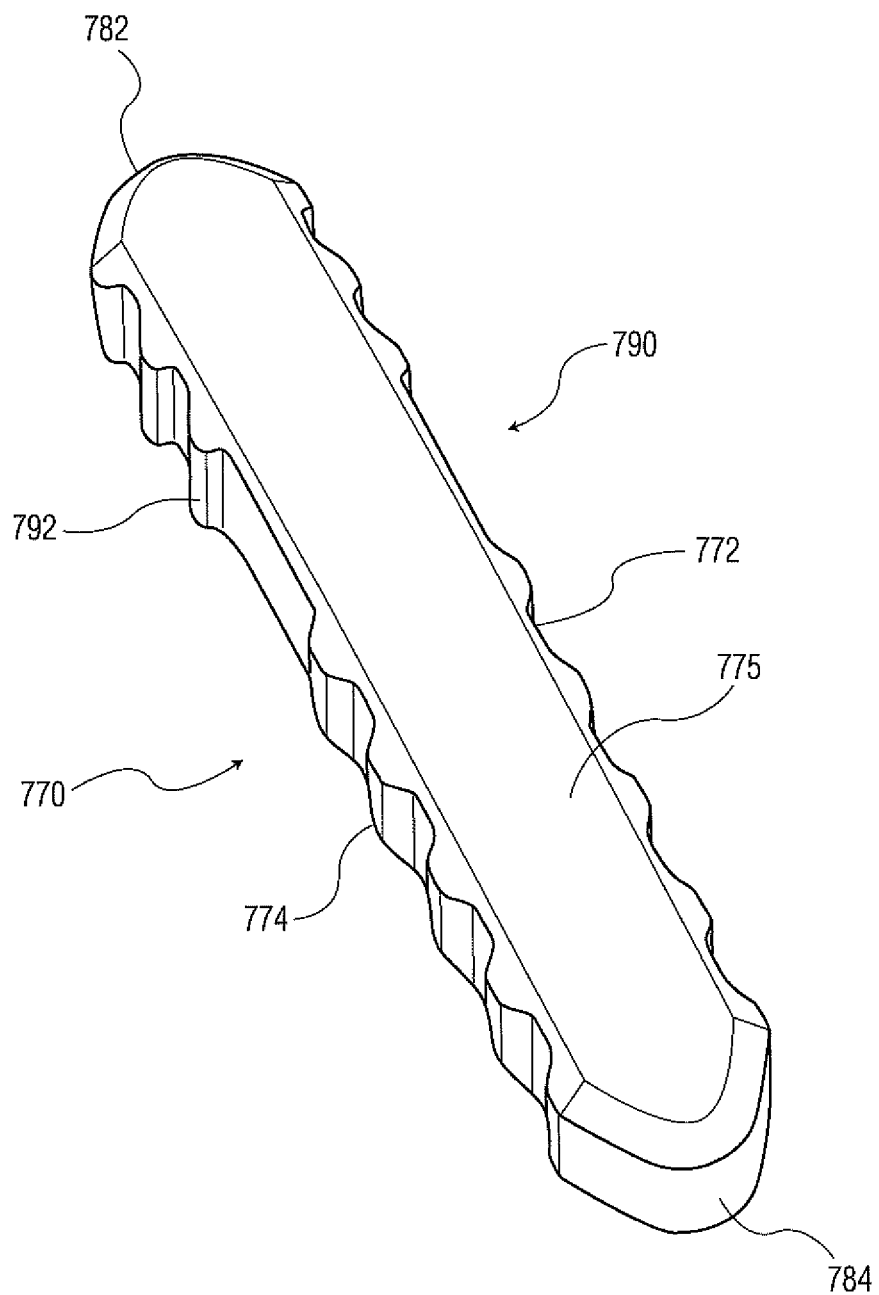
FIG. 36 is a perspective view of a bone implant in accordance with still another embodiment of the present disclosure.
Figure 37:
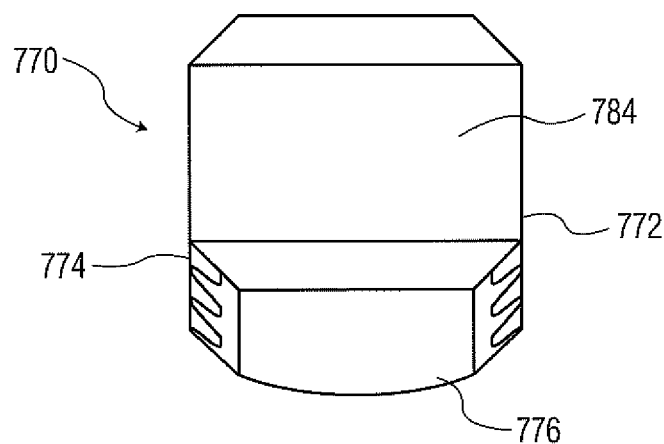
FIG. 37 is a front view of the bone implant of FIG. 36.
Figure 38:
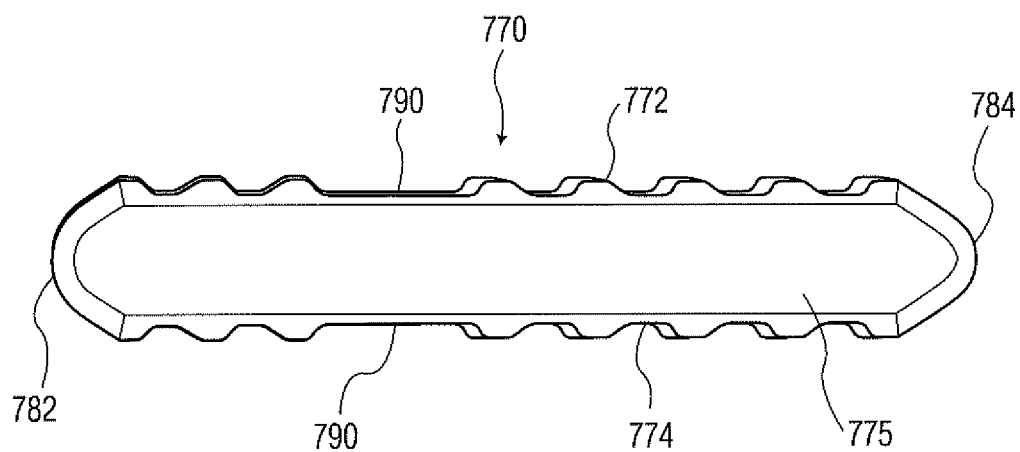
FIG. 38 is a side view of the bone implant of FIG. 36.
Figure 39:
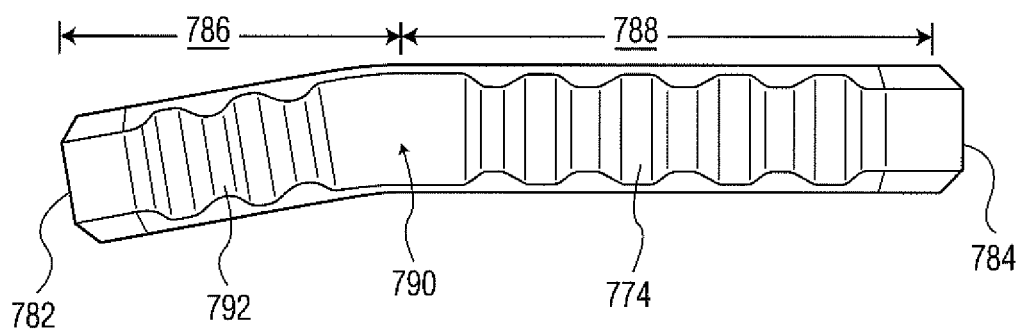
FIG. 39 is a top view of the bone implant of FIG. 36.

In another embodiment, FIGS. 35A and 35B illustrate implant 670 having some of the features of the implant of FIGS. 28-34. However, implant 670, similar to implants 170, 370 above, includes a distal portion 686 and a proximal portion 688 that extend along axes that are transverse to one another. While the angle or bend in the implant may be positioned adjacent to or at engaging surface 690, it may be positioned anywhere desired.

Figure 44:
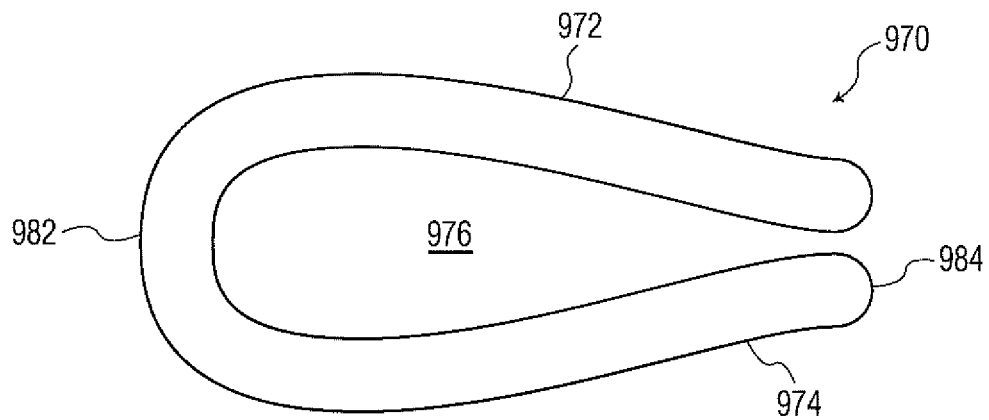
FIG. 44 is a top view of a bone implant in accordance with another embodiment of the present disclosure.

In a further embodiment, FIG. 44 provides a sketch of implant 970 having some of the features of the implant of FIGS. 1-4. However, while implant 970 includes a monolithic construction, and generally includes the same features and shapes as implant 70, 170, first portion 972 and second portion 974 are only continuous with one another at the proximal end 982 and are spaced from one another at the distal end 984.

Figure 45:
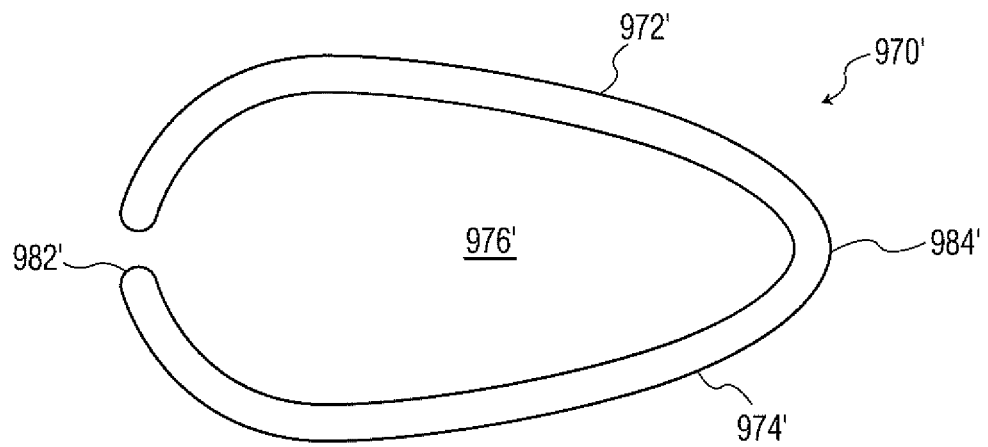
FIG. 45 is a top view of a bone implant in accordance with yet another embodiment of the present disclosure.

In another embodiment, FIG. 45 provides a sketch of implant 970' which is largely similar to implant 970, except that the first portion 972' and second portion 974' are only continuous with one another at the distal end 984' and are spaced from one another at the proximal end 982'.

As with other implants discussed above, upon compression of either implant 970 or implant 970', the ends spaced from one another move towards one another to create a smaller cross-section which may be suitable for insertion of the implant into bone, as discussed above.

Figure 46:
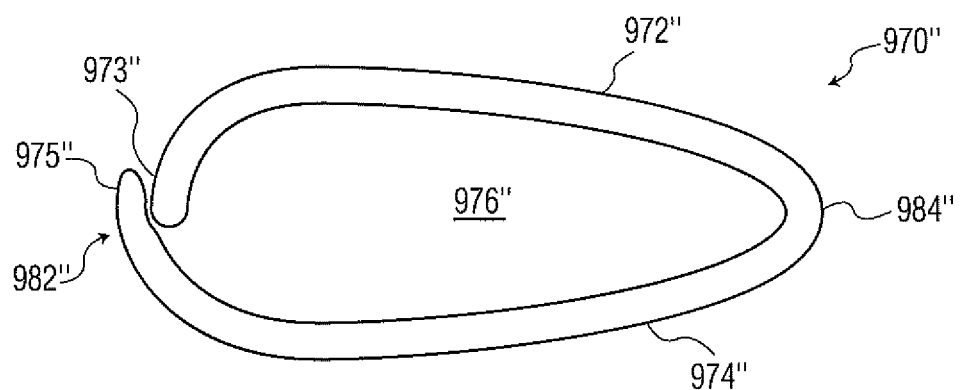
FIG. 46 is a top view of a bone implant in accordance with still another embodiment of the present disclosure.

In yet another embodiment, FIG. 46 provides a sketch of implant 970" which is largely similar to implant 970', and as such the first portion 972" and second portion 974" are only continuous with one another at the distal end 984" and are spaced from one another at the proximal end 982". However, ends 973", 975" of the first and second portions of implant 970" interact with one another. For instance, as illustrated, end 973" tucks within end 975". The ends in this configuration may have corresponding shapes to promote nestling of end 973" against end 975" (e.g., matching concave and convex surfaces). Such interaction of the ends may help maintain alignment of the portions 972", 974" during compression by lessening the chance that the end move laterally relative one another and slide past one another. Further, if for example, end 975" extends fully around end 973", the extension of end 975" may prevent end 973" from bending outwards when compression is applied on the midsection of the implant.

While FIGS. 44-46 are sketches, it should be understood that each of these implant embodiments are generally flat in shape and may also include additional structures such as barbs 92, flanges 78, 80 and other such structures illustrated with respect to implant 70, 170. Further, each of these implants 970, 970', 970" can be manipulated, handled and implanted as discussed above relative to implant 70, 170. Still further, each of these implants can include an angle as discussed above relative to FIGS. 5-7.

Further, FIGS. 44-46 may be constructed of metal, such as titanium, Nitinol, stainless steel, or the like. The open end may reduce the overall strength of the implant such that the metal structure can be more easily flexed/compressed for insertion into bone.

Figure 47:
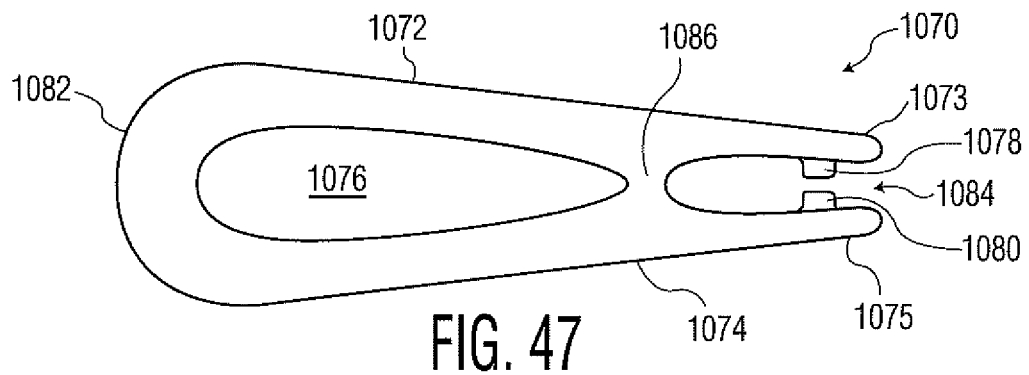
FIG. 47 is a top view of a bone implant in accordance with another embodiment of the present disclosure.

In another embodiment, as illustrated in FIG. 47, implant 1070 includes a first portion 1072 and a second portion 1074 connected at a proximal end 1082 and at an intermediate location 1086. The first and second portions also include ends 1073, 1075, respectively, which extend from the intermediate location to a distal end 1084. The ends 1073, 1075, can also include flanges 1078, 1080, respectively, Implant 1070 may be compressed at two separate locations on either side of the intermediate location 1086, typically prior to insertion of each end into a bone. For instance, the proximal side with opening 1076 can be compressed for insertion of the proximal side into bone, and the distal ends 1073, 1075 can be compressed for insertion of the distal side into bone. The flanges 1078, 1080 may limit compression of ends 1073, 1075 as discussed above relative to implant 70.

Figure 48:
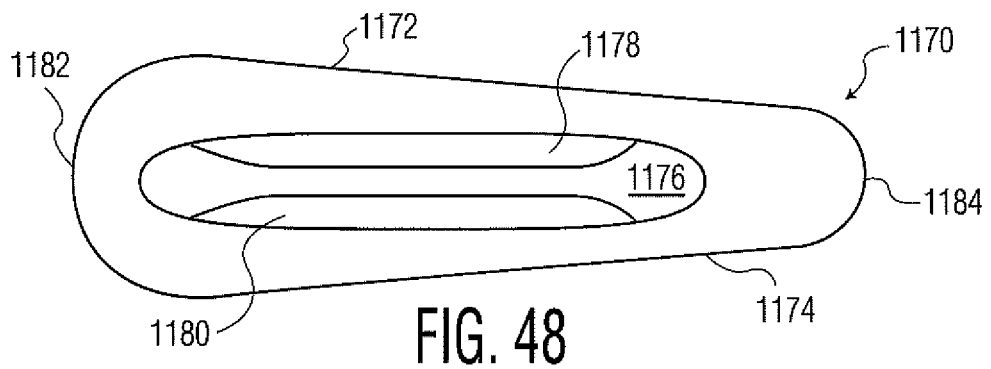
FIG. 48 is a top view of a bone implant in accordance with another embodiment of the present disclosure.

In still another embodiment, FIG. 48 illustrates implant 1170 having a first portion 1172 and a second portion 1174 connected at a proximal end 1182 and a distal end 1184 in similar fashion as implant 70 discussed above. Implant 1170 further includes a bullet nosed distal end 1184 which includes additional material versus implant 70. Such additional material can be beneficial where implant 1170 is formed of plastic, such as PEEK, which has ample flexibility. The added material in distal end 1184, which is smaller in size than the proximal end 1182, increases strength of the distal end 1184 and may limit some flexibility of the distal portion of the implant which may improve fixation of the implant in the bone. Implant 1170 also can include a flange or flanges 1178, 1180 extending into opening 1176, similar to the flange(s) and opening in implant 70. Optionally, implant 1170 (and indeed, any of the embodiments discussed herein) can include a cannulation suitable for passage of the implant onto a guidewire.

Figure 49:
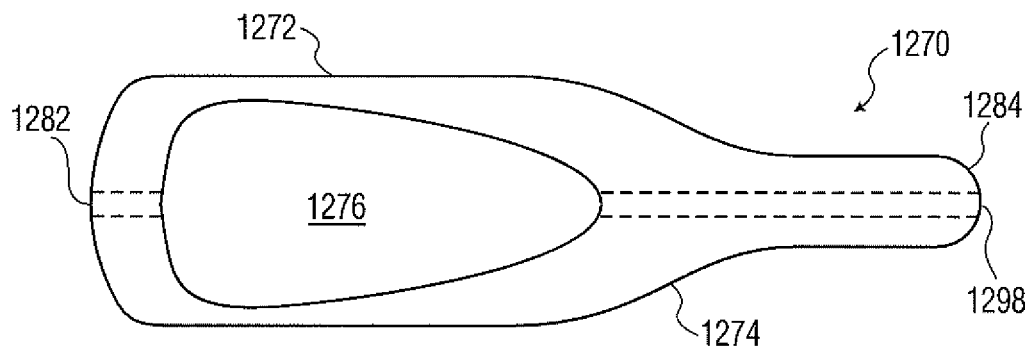
FIG. 49 is a top view of a bone implant in accordance with another embodiment of the present disclosure.

In another embodiment, FIG. 49 illustrates implant 1270 which is similar to implant 1170 (and like reference numbers denote like structures), above, in that it includes a bullet-shaped distal end 1284, though distal end 1284 has a narrower shape than distal end 1184 of implant 1170. Also illustrated is the optional cannulation 1298 for passage of the implant over a guidewire. During insertion, an operator would compress first and second portions 1272, 1274 along opening 1276 for insertion of the proximal end 1282 into bone, while distal end 1284 may simply be press-fit into bone.

Figure 50:
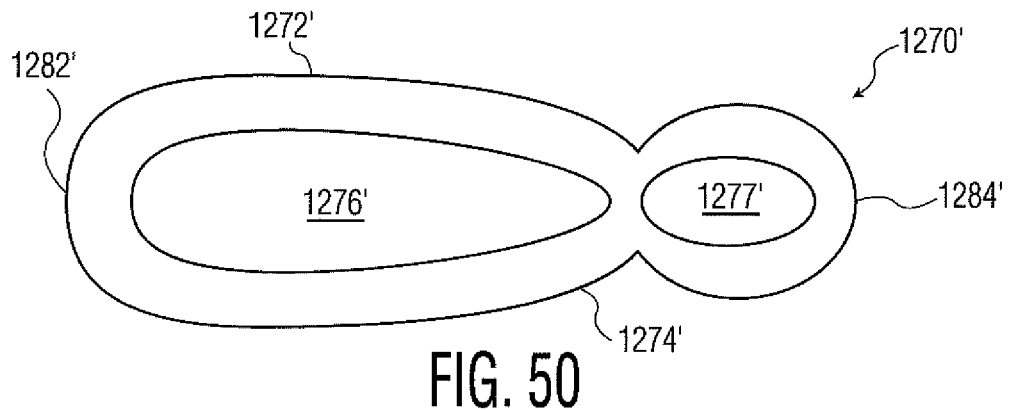
FIG. 50 is a top view of a bone implant in accordance with another embodiment of the present disclosure.

In yet another embodiment, FIG. 50 illustrates implant 1270' which is similar to implants 1170, 1270 (and like reference numbers denote like structures), but instead of a bullet-shaped distal end 1184, 1284, the distal end 1284' is rounded and includes a second opening 1277' therein. Contrary to implant 1270, above, distal end 1284' in this instance may also be compressed by the operator for insertion into bone, though a simple press-fit technique may still be suitable.

The various implants illustrated in FIGS. 47-50 may be formed of plastic, such as PEEK. PEEK has greater flexibility than, for example, metal (e.g., as used in the implants of FIGS. 44-46), and thus the addition of material to the structure may help to increase strength and decrease some of the flexibility such that the anchor can still be flexed or compressed for insertion into bone, but also have the strength to maintain its position in bone.

While FIGS. 47-50 are sketches, it should be understood that each of these implant embodiments are generally flat in shape and may also include additional structures such as barbs 92, flanges 78, 80 and other such structures illustrated with respect to implant 70, 170. Further, each of these implants 1070, 1170, 1270, 1270' can be manipulated, handled and implanted as discussed above relative to implant 70, 170. Still further, each of these implants can include an angle as discussed above relative to FIGS. 5-7.

In still another embodiment, the implant of the present disclosure can be constructed of allograft. For instance, as illustrated in FIGS. 36-39, implant 770 includes a first side surface 772 and a second side surface 774 and a top surface 775 and bottom surface 776, though it is noted that the final positioning in bone does not require any particular orientation. At least one of the surfaces can include at least one barb 792, and as an example, as illustrated, barbs are only on side surfaces 772, 774.

Implant 770 may be constructed of any material desired, and preferably the implant body is constructed of allograft. While implant 770 does not have a spring-like structure, like the other embodiments disclosed herein, the allograft substance itself can be designed to have a degree of compressibility. For instance, including a higher amount of cancellous bone and less cortical bone could allow for increased compressibility, while a higher amount of cortical bone can be used to create a harder implant that can better maintain a specific orientation of the bones relative to one another. The allograft may also optionally be demineralized in a portion or throughout the implant body to provide further compressibility. In this instance, the implant would be partially demineralized such that the implant has a degree of compressibility while still maintaining strength. Further, various surface features, such as barbs and the like, or throughbores or other structures may be manufactured into the implant as desired to generate beneficial effects such as increased resistance to pullout, increased bone ingrowth, and the like.

While compression of the implant 770 may not be necessary for insertion, the implant can still include an engagement surface 790 along the length of the implant for interaction with a tool for insertion or removal.

Implant 770, as illustrated, includes a bend or angle, similar to implants 170, 370, 670 above, such that a proximal portion 788 extends along a first axis and a distal portion 786 extends along a second axis transverse to the first axis. However, as with the other embodiments herein, implant 770 may also be linear.

Since the ends of the implant 770 do not require compression, the method of insertion may include, in one embodiment, preparing the first and second bones as discussed above. With the bones prepared, the implant is then inserted into one of the bones first and then into the second bone. Each time, the implant is pressed into the bone until the bone is adjacent to or contacts the insertion tool at engagement surface 790. Generally, the allograft of implant 770 has a degree of compressibility such that implant 770 is inserted into the bones by press-fit. For instance, the implant is pressed into each bone via a force applied to the inserter such that the ribs (if present) deflect as they pass into the bone. Once the implant is in position, the ribs, or the body of the implant itself, serve to inhibit removal of the implant from the bone. The inserter is then removed from the implant and any space between the bones is reduced by manual compression.

Figure 40A:
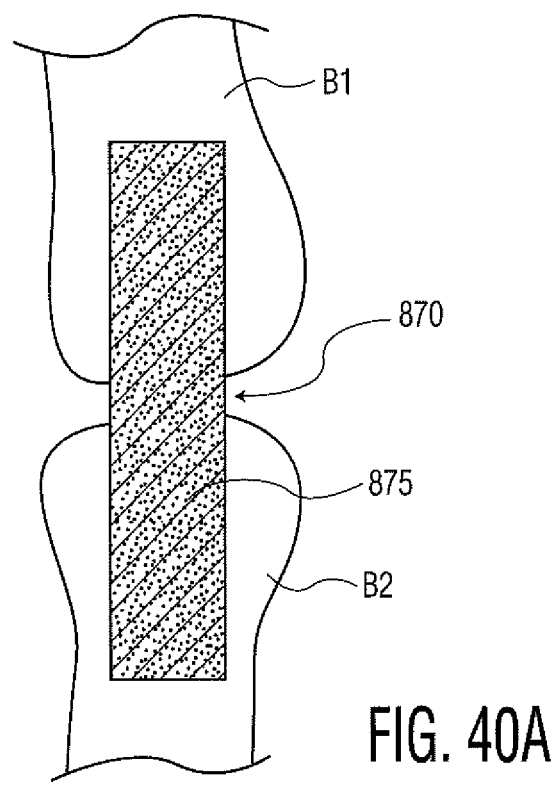
FIGS. 40A and 40B illustrate another embodiment of a bone implant in first and second bones.
Figure 40B:
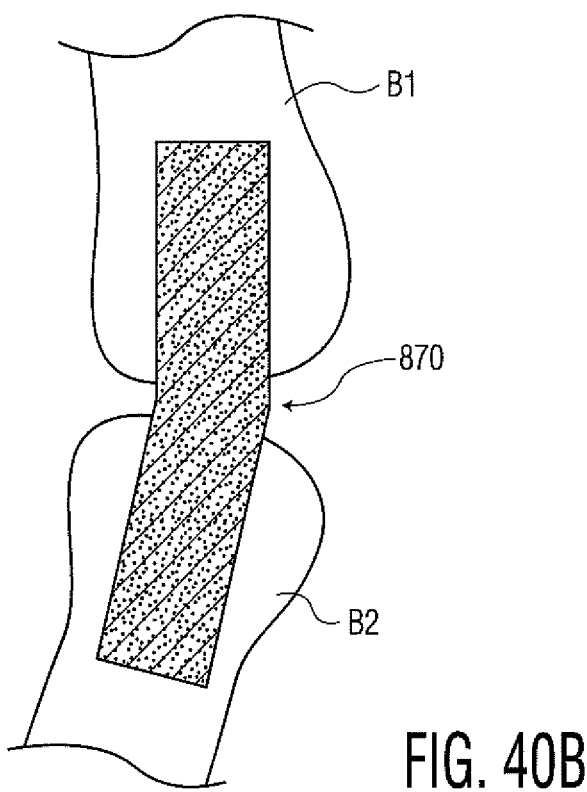
Figure 41:
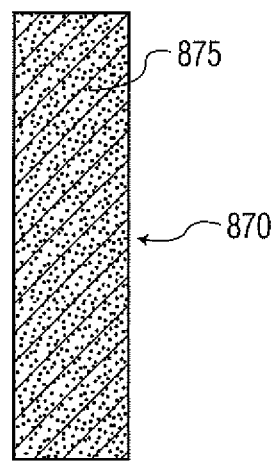
FIGS. 41-43 illustrate alternative embodiments to the bone implant of FIGS. 40A and 40B.

In yet a further embodiment, an implant of the present disclosure can be constructed of a porous material, such as a porous metal. For instance, FIGS. 40A-B and 41 illustrate another embodiment of an implant 870 including a body 875 that is at least partially constructed of a porous material, such as a porous metal structure. As illustrated, the body 875 can be completely formed of porous material.

Figure 42:
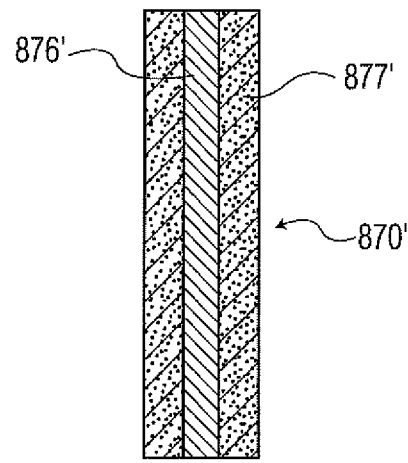

FIG. 42 illustrates an alternative implant 870' which includes a porous portion 877' and a nonporous portion 876', illustrated as a nonporous spine or core, though the nonporous and porous portions can have any configuration in the longitudinal and/or latitudinal directions. Further, the implant could include multiple nonporous portions present within the body of the implant. These nonporous portion or portions might provide additional support to the implant structure.

As with implant 770, the porous or partially porous body 875 of implant 870 can promote bone ingrowth and integration into the implant. The degree of porosity and amount of the body forming the porous portion can all be varied to provide for the desired amount and location of bone ingrowth. Further, the porous portions of the implant may provide a spring-like structure to the implant, as discussed above relative to implant 770.

The porous portion can be constructed as is known in the art, for example through negative manufacturing techniques such as laser etching, or additive manufacturing techniques such as powder metallurgy, stereolithography, 3-D printing, selective laser melting (SLM), additive layer manufacturing (ALM), tessellation, other pore forming or metallic foam manufacturing techniques, or the like. Examples of additive manufacturing techniques which can be used in forming such a porous portion include U.S. Pat. Nos. 9,403,213; 7,537,664; 8,992,703; 8,728,387; 9,135,374; 7,674,426; 9,089,431; 9,089,427; and 9,180,010; U.S. Published App. No. 2006/0147332; and U.S. application. Ser. No. 14/969, 695—all of which are incorporated by reference herein as if fully set forth herein. Further, any metal or polymer may be utilized in forming the implant such as commonly used titanium, stainless steel, PEEK, resorbable polymers, and the like.

Figure 43:
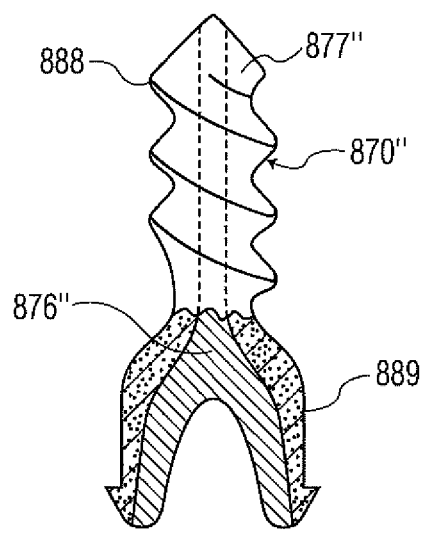

The shape of implant 870 can be any shape desired. FIGS. 40-42 illustrate rectangular cuboid shapes, while FIG. 43 illustrates a unique shape that includes a threaded portion 888 and a portion 889 extending into multiple arms. Other shapes are also envisioned. Additionally, the rectangular cuboid implant 870 can also optionally include a bend or angle, as in FIG. 40B, and as discussed in other embodiments above. Still further, as illustrated for example in FIG. 43, the implant 870" could include at least one barb and/or thread, or other such structure, to improve fixation with the surrounding bone.

Implant 870 may be implanted in similar fashion as implant 770, described above, that is, via press-fit. FIGS. 40A-B illustrate an example of the implant 870 being positioned in first and second bones B1, B2.

Figure 54:
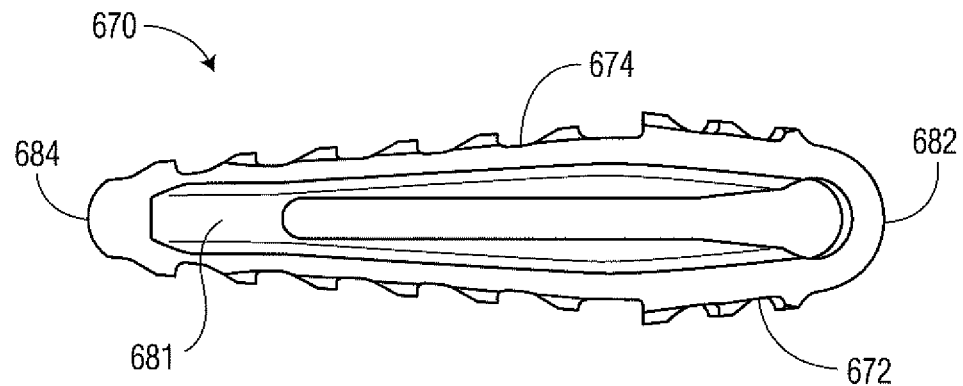
FIG. 54 is a top view of a bone implant according to a further embodiment of the present disclosure.

FIG. 54 depicts a bone implant 670 according to another embodiment of the present disclosure. Implant 670 is similar to implant 70 in that it includes first and second portions 672, 674 separated by a gap and proximal and distal ends 682, 684 connecting said first and second portions 672, 674. However, implant 670 differs from implant 70 in that implant 670 is constructed from a polymer material such as PEEK, for example. As discussed above with regard to implant 1170, such a polymer implant may have more material at one of its ends to provide additional rigidity. In this regard, while implant 670 includes a substantially uniform wall thickness at its proximal end 682, the distal end 684 includes a web 681 that extends in a proximal-distal direction. Such webbing 684 also helps provide strength to implant 670 as it is press-fit into a bone.

Figure 55A:
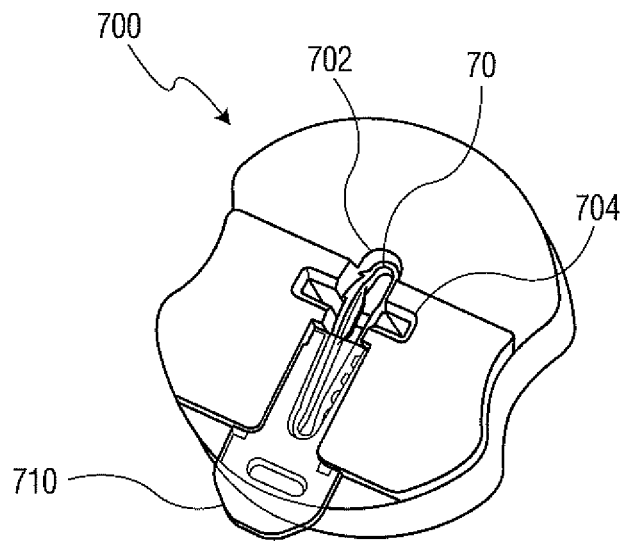
FIG. 55A is a perspective view of an implant loading device according to an embodiment of the present disclosure.

FIG. 55A depicts an implant loading device or implant loading puck 700 according to an embodiment of the present disclosure. Loading device 700 may be used to help load implant 70, or other implants disclosed herein, onto clip 106. In this regard, loading device includes a body with a first recess 702 that has a general shape of implant 70. Thus, first recess 702 can be angled to conform to straight implant 70 or angled implant 170 (discussed above). A second recess 704 intersects first recess 702 and is shaped to receive arms 108 at a distal end of clip 106. Moreover, second recess 704 intersects first recess 702 at a predetermined location such that when implant 70 is disposed in first recess 702, second recess 704 aligns with engagement surface 90. In this regard, inserting the distal end of clip 106 into second recess 704 guides clip 106 into engagement with implant 70 at the desired location.

Loading device 700 also includes a removable lid 710 that helps prevent implant 70 from being inadvertently removed from first recess 702. As shown, lid 710 is configured to slide within slots (not shown) at opposite sides of first recess 702 so as to selectively cover first recess 702. In addition, lid 710 can be positioned so that it covers a portion of implant 70 disposed within first recess 702 while not obstructing second recess 704 so that implant 70 can be engaged with clip 106. Once implant 70 is secured to clip 106, lid 710 can be slidably removed from device 700 thereby uncovering first recess 702 and allowing implant 70 to be removed. Although a sliding lid is shown, other selectively removable retaining configurations are also contemplated, such as lid that snaps onto device with a snap-fit feature, a cover having an adhesive surface, or the like as is commonly understood in the art.

Figure 55B:
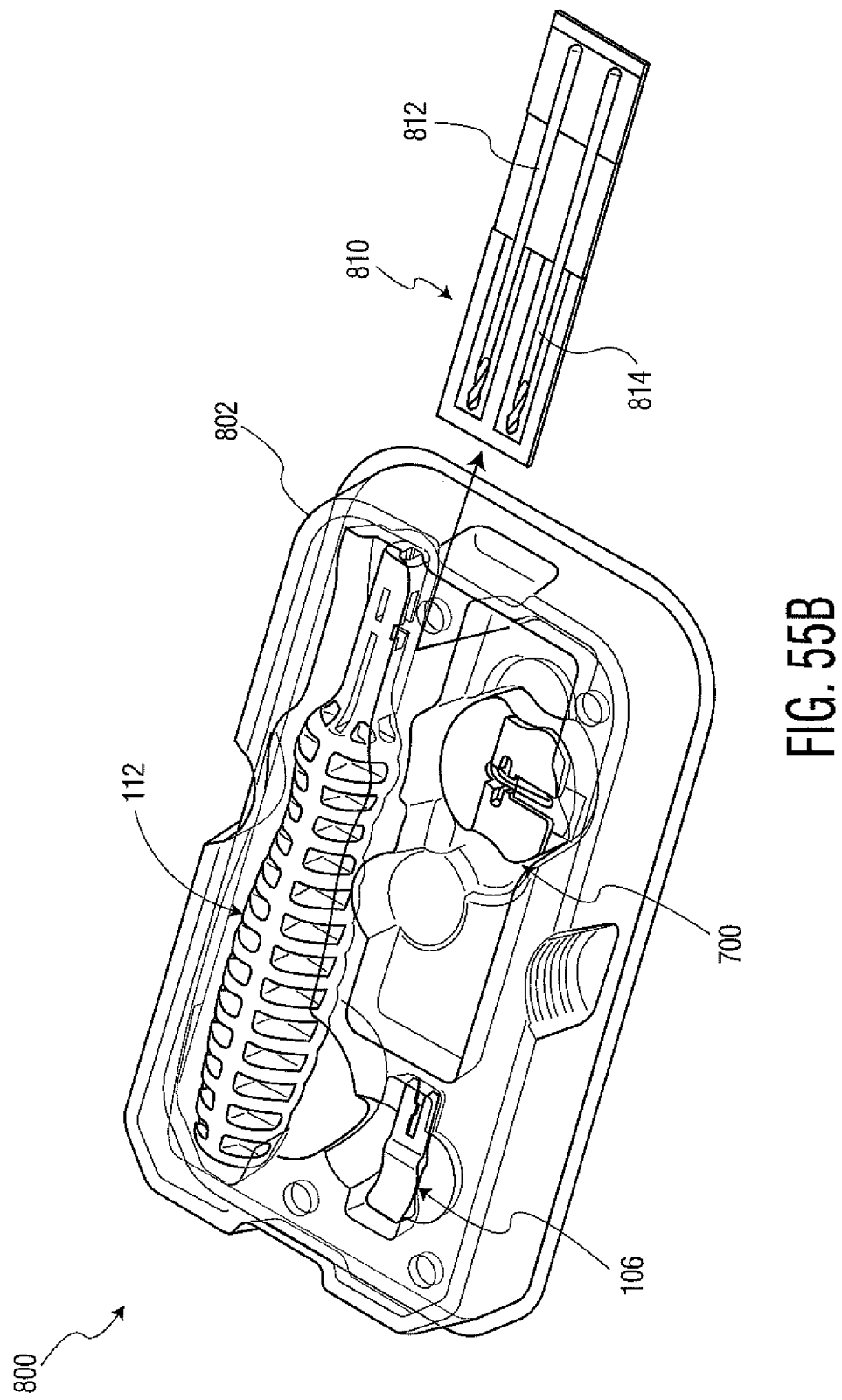
FIG. 55B is a perspective view of an implant kit according to an embodiment of the present disclosure.

In other embodiments, a kit can be formed from one or more implants and instruments. One such example is a kit 800 depicted in FIG. 55B. As shown, kit 800 includes an inner shell 802, inserter handle 112, clip 106, loading device 700, implant 70 within device 700, and cutting tools 812, 814 (e.g., drill bits). Inner shell or blister 802 may also include an inner shell cover (not shown). Inner shell 802 and inner shell cover may be provided in an outer shell/blister (not shown) with a peelable membrane. Inner shell 802 includes various compartments for sterilization and transport of each component mentioned above. In addition, loading device 700 may be preloaded with implant 70, or another one of the implants described herein. Alternatively, one or more bone implants can be provided in a separate compartment and may be loaded into loading device 700 within the operating theater.

In a further kit embodiment, a kit may include at least one combination of an implant secured to a tool, such as clip 106, for use in insertion of the implant. The combination of implant secured to the tool can be packaged in this fashion. Alternatively, the package could include at least one implant and at least one tool therein for subsequent connection.

In another kit embodiment, a kit could include a container with individually packaged implants and at least one individually packaged tool. The tool could be universal to all implants or separate tools could be available for use with certain implants in the container. In another variation, such a kit could include a first container with at least one implant (packaged individually or as a group), and a second container with at least one tool (packaged individually or as a group). Further, either of the containers could include other instruments, such as one or more of a drill, a guide (such as a K-wire), a bone shaver or cutter, and the like.

Other combinations of kits, including those including more than one implant of a particular embodiment above, or those including various embodiments of the implants above, are also envisioned. For example, a kit can include at least one implant 70 and multiple implants 170 having various angles such that an operator can select a particular angle of implant for use in a particular procedure. Any of the above kits may further include a surgical procedure which may include instructions or protocol for selecting and using the elements of the particular kit.

Figure 56A:
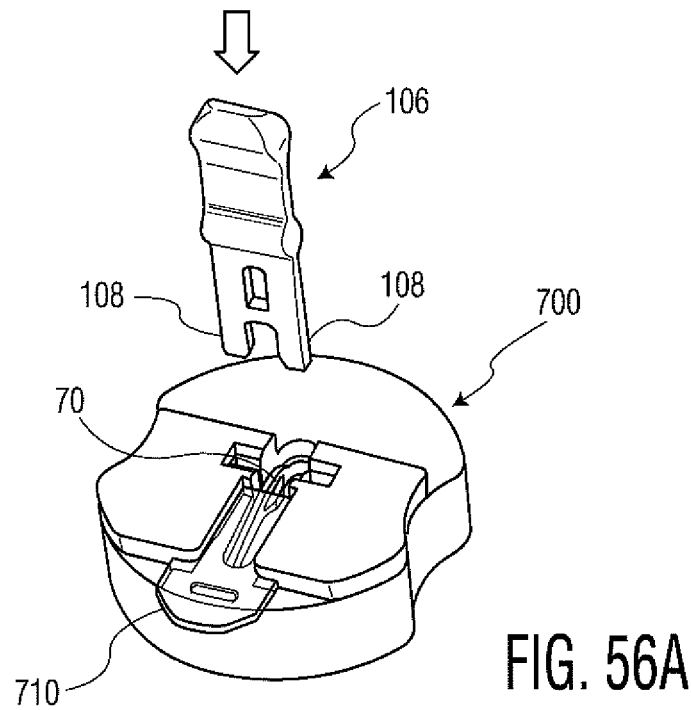
FIGS. 56A-E a method of implanting the bone implant of FIG. 1 according to an embodiment of the present disclosure.
Figure 56B:
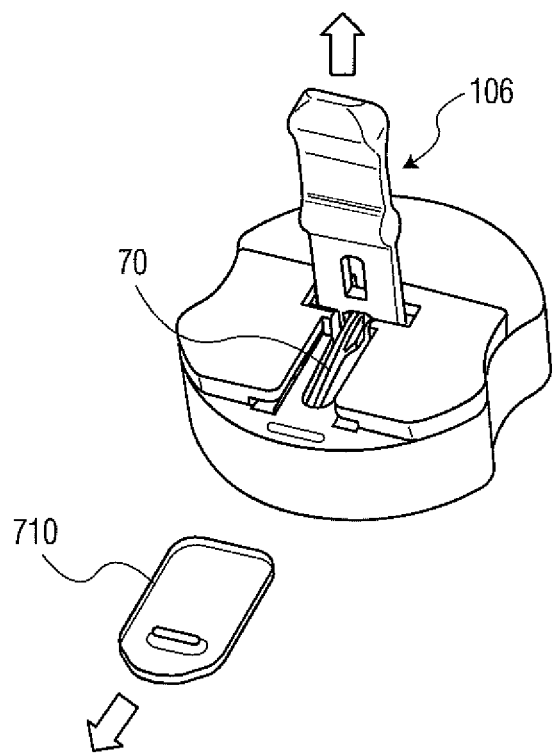

FIGS. 56A-56B depict a method of implantation using the components of kit 800. In the method, after all components 106, 112, 700, and 810 are removed from the kit container, drills 812, 814 are used to form openings in respective proximal and distal bone fragments B1, B2. In addition, bone implant 70 is connected to clip 106. In this regard, lid 710 may be slid rearward to expose second recess 704 or, in some embodiments, lid 710 may already be positioned so as to not cover second recess 704 while still covering a portion of first recess 702. Clip 106 is then inserted into second recess 704 as shown in FIG. 56A such that arms 108 of clip 106 engage respective first and second portions 72, 74 of bone implant 70 at the engagement surface 90 thereof. As clip 106 is advanced into the second recess 704, angled portions 110 of arms 108 push first and second portions 72, 74 toward each other so as to position first and second portions 72, 74 into a compressed state. The bias of the first and second portions 72, 74 against arms 108 of clip 106 help secure bone implant 70 to clip 106. During engagement of clip 106 to bone implant 70, lid 710 helps prevent the distal end 84 of bone implant 70 from popping out of first recess 702.

Figure 11A:
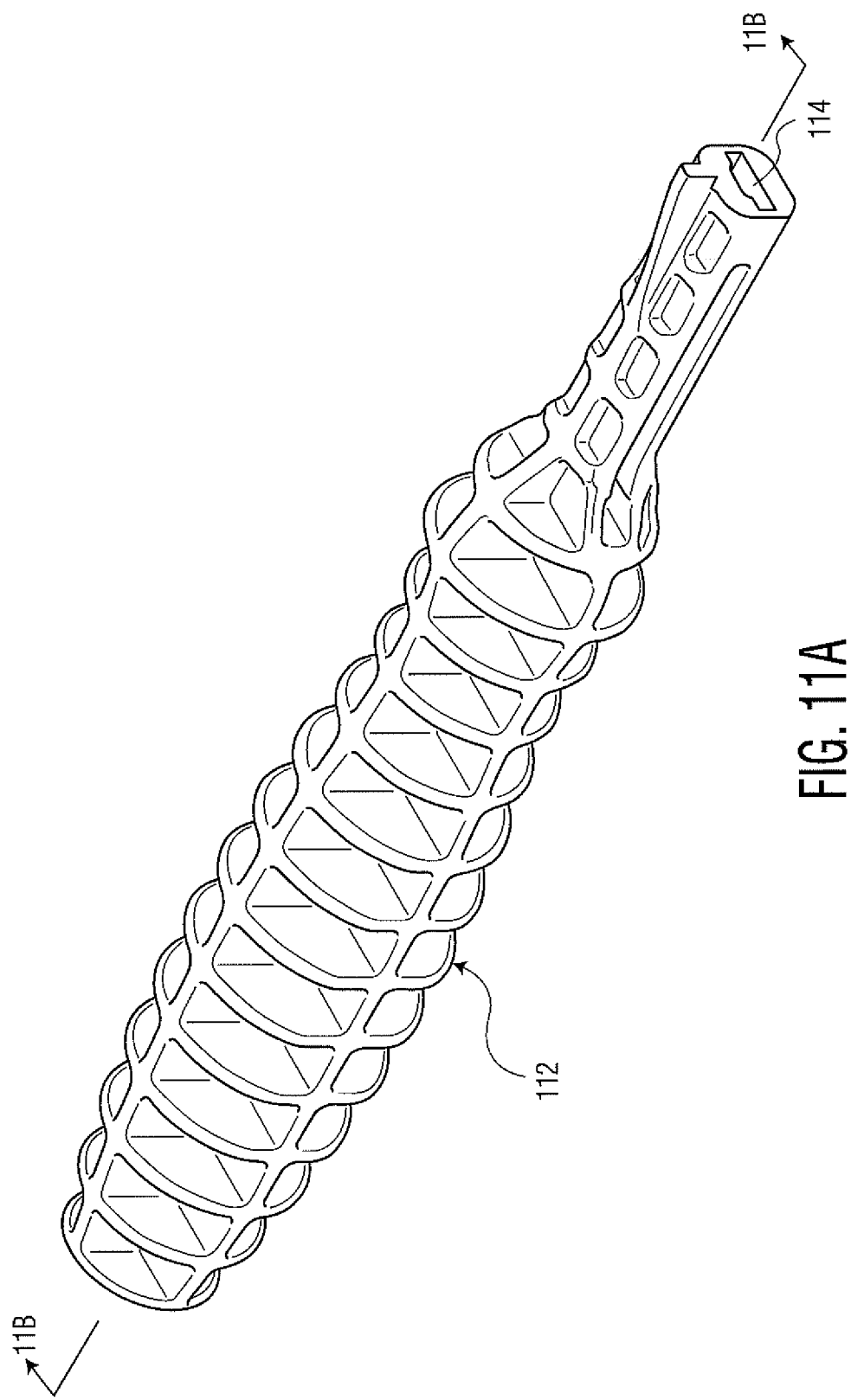
FIG. 11A is a perspective view of one embodiment of an instrument.
Figure 11B:
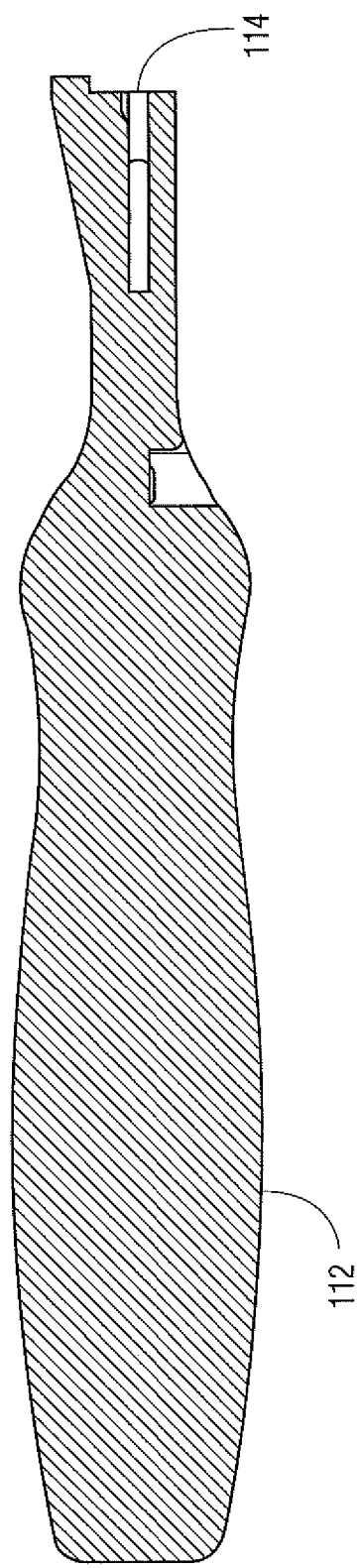
FIG. 11B is a cross-section view of the instrument of FIGS. 11A and 11D.
Figure 11C:
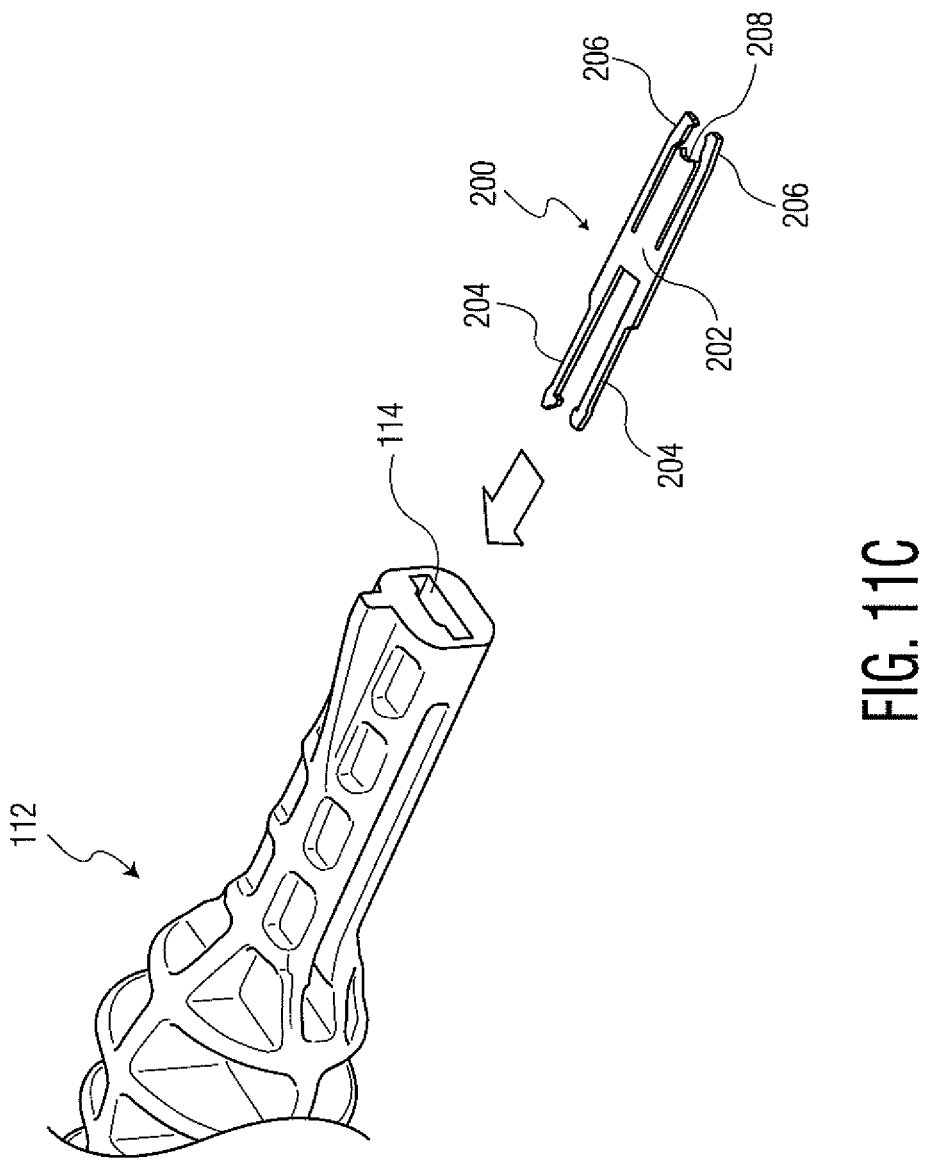
FIG. 11C is a perspective view of a distal end of such instrument including an insert that for receipt in said distal end.
Figure 11D:
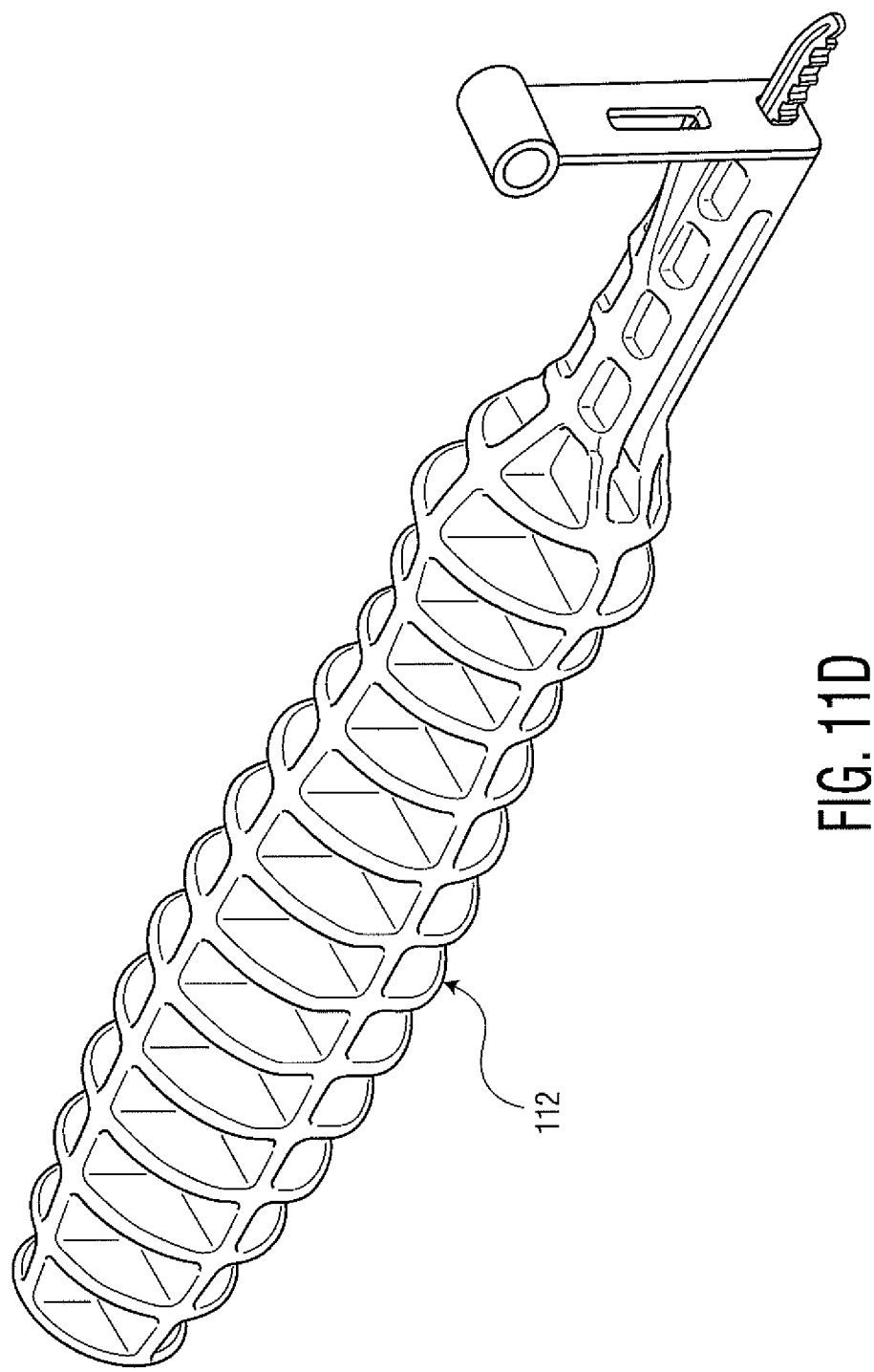
FIG. 11D is a perspective view of the instrument coupled to the clip of FIG. 8 which is coupled to the bone implant of FIG. 1.
Figure 56C:
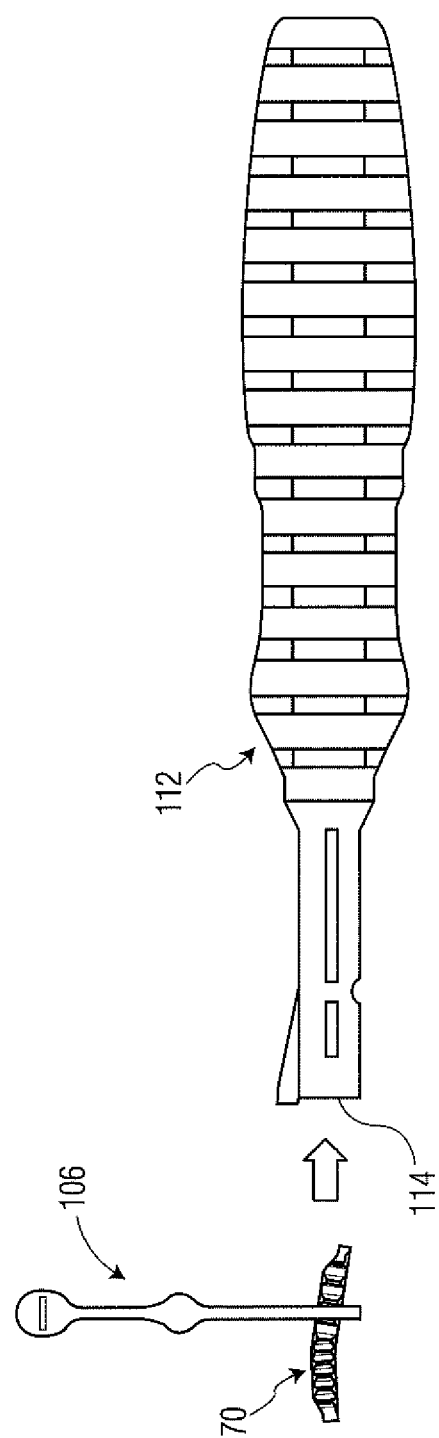

Once bone implant 70 is secured to clip 106, lid 710 is removed from loading device 700 and clip 106 is lifted out of loading device 700 along with bone implant 70, as best shown in FIG. 56B. Thereafter, proximal end 82 of bone implant 70 is loaded into the distal end of inserter handle 112, as shown in FIG. 56C. In this regard, proximal end 82 of implant 70 is inserted into opening 114 and between arms of insert 200 until implant 70 abuts an abutment surface 208 of body 202. As this occurs, arms 206 flex outward and pinch implant 70 therebetween to securely hold implant 700. Clip 106 remains attached to implant 70 and is positioned adjacent distal end of handle 112, as best shown in FIG. 11D.

Figure 56D:
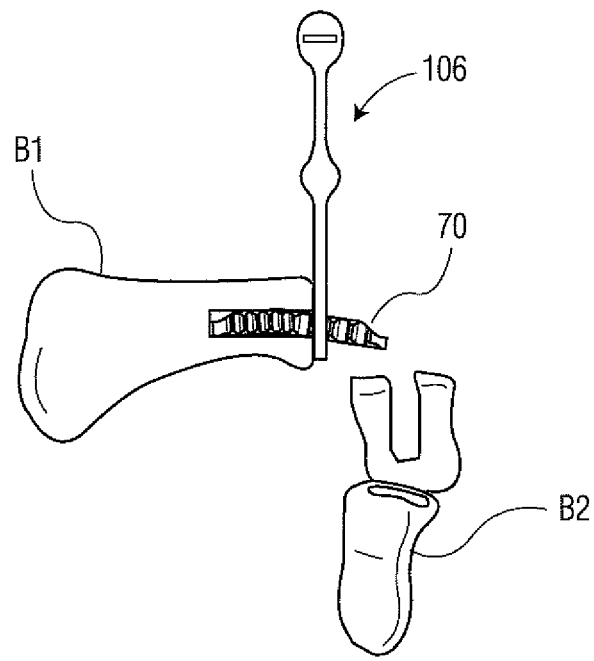
Figure 56E:
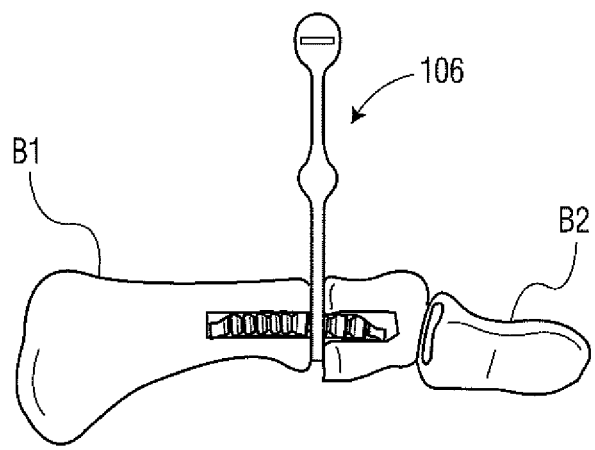

Once implant 70 is secured to distal end of inserter handle 112, implant 70 can be inserted into bone B1. In this regard, inserter handle 112 is manipulated so as to insert distal end 84 of implant 70 into proximal bone B1, which may be performed in a press-fit manner. Thereafter, handle 112 is detached from implant 70 by pulling handle 112 in an opposite direction. At this point, the distal end of clip 106 is positioned adjacent bone B1, as shown in FIG. 56D. Proximal end 82 of implant 70 is then placed into distal bone B2, as shown in FIG. 56E. At this point, clip 106 which has a narrow thickness, is positioned between bones B1 and B2. The clip 106 is then removed, which allows first and second portions 72, 74 to move toward their uncompressed state. As this occurs, first and second portions 72, 74 push firmly against bones B1 and B2 causing barbs 92 to bite into the bone to prevent removal therefrom. However, due to the angle of the barbs 92, bone B2 can be pushed against bone B1 and moved relative to implant 70 to close the space left by clip 106.

To summarize the foregoing description, a bone implant may include a proximal end; a distal end; a first portion extending between the proximal and distal ends having a maximum portion height and a minimum portion height; a second portion extending between the proximal and distal ends having a maximum portion height and a minimum portion height, the second portion connected to the first portion at the proximal end and the distal end and the second portion moveable with respect to the first portion to transition the bone implant between a relaxed state wherein the first and second portions are separated by a first distance and a contracted state wherein the first and second portions are separated by a second distance different from the first distance; and at least one of the proximal end and the distal end having the minimum portion height; and/or the bone implant may also include an anchor element on at least one of the first portion and the second portion; and/or the bone implant can be transitioned to or maintained in the contracted state via engagement with an instrument at a single contact point on each of the first portion and the second portion; and/or the proximal end is oblique to the distal end; and/or the bone implant may include a first flange extending from the first portion towards the second portion and a second flange extending from the second portion towards the first portion; and/or the first and second flange members are spaced from one another when in the relaxed state and contact one another when in the contracted state; and/or a proximal end width is greater than a distal end width; and/or the first and second portions define a channel extending between the first and second portions and towards the proximal and distal ends, the channel adapted to accept a guide wire therein.

Also described is a bone implant system which may include: a monolithic bone implant including a proximal end, a distal end, a first portion extending between the proximal and distal ends, a second portion extending between the proximal and distal ends, and a channel extending between the first and second portions and towards the proximal and distal ends; and a guide wire adapted to be positioned along the channel, wherein, with the guide wire positioned along the channel, the bone implant is adapted to travel along the guide wire to an implantation site.

Also described is a method of implanting a bone implant, which may include: obtaining a monolithic bone implant including a first portion connected to a second portion at a proximal end and a distal end; engaging the implant with an instrument at a single point of contact on each of the first and second members to transition the bone implant from a relaxed state where the first portion is separated from the second portion by a distance to a contracted state where the first portion is separated from the second portion by a reduced distance; with the bone implant in the contracted state, inserting the proximal end of the bone implant into a first bone portion; with the bone implant in the contracted state, inserting the distal end of the bone implant into a second bone portion; and disengaging the insertion instrument from the bone implant to allow the bone implant to return to the relaxed state; and/or the bone implant includes a channel extending between the first and second portions and towards the proximal and distal ends, wherein, prior to the step of inserting the proximal end of the bone implant into the first bone portion, the method further comprises the step of implanting a guide wire into the first bone portion, and the step of inserting the proximal end further comprises positioning the guidewire through the channel and moving the bone implant along the guidewire and into the first bone portion; and/or with the guidewire positioned through the channel, the guidewire contacts at least two of the proximal end, the distal end, and first and second flanges, the first flange extending from the first portion towards the second portion and the second flange extending from the second portion towards the first portion; and/or the method may include the steps of: reengaging the implant with the instrument; transitioning the implant from the relaxed state to the contracted state; and removing at least one of the proximal and distal ends of the implant from the bone; and/or the inserting the proximal end step includes inserting the proximal end into a proximal phalanx and the inserting the distal end step includes inserting the distal end into a middle phalanx; and/or the first portion includes a first flange and the second portion includes a second flange and the engaging step includes transitioning the bone implant to the contracted state such that the first flange is adjacent the second flange; and/or the method may include the step of positioning at least a portion of the first flange and second flange between the first bone portion and the second bone portion; and/or the bone implant includes a proximal end portion and a distal end portion, the distal portion oblique to the proximal portion, and the step of inserting the distal end includes orienting the second bone oblique to the first bone; and/or the bone implant includes a proximal end portion and a distal end portion and the method further comprises simultaneously transitioning the proximal end portion and the distal end portion to the contracted state by engaging the bone implant with the insertion instrument.

Also described is a bone implant, which may include: a proximal end; a distal end; a first portion; a second portion connected to the first portion at the proximal and distal ends of the bone implant; a first flange extending from the first portion towards the second portion; and a second flange extending from the second portion towards the first portion, wherein the implant can be transitioned between a relaxed state where the first flange and second flange are separated by a first distance and a contracted state wherein the first flange and the second flange are separated by a second distance different from the first distance; and/or the first and second portions have a portion height and the first and second flanges have a flange height smaller than the portion height; and/or the implant may include a channel defined between the first and second portions, the channel having a height defined by the difference between the portion height and the flange height; and/or the first and second portions include a portion height and at least one of the proximal and distal ends of the bone implant have an end height smaller than the portion height; and/or the implant may include a channel defined between the first and second portions and within the portion height, and the channel ending above the end height at the proximal and/or distal end; and/or the implant may include a first anchor on the first portion to prevent movement of the bone implant in a first direction; and a second anchor on the first portion to prevent movement of the bone implant in a second direction; and/or the implant includes a proximal end portion extending along a proximal axis and a distal end portion extending along a distal axis transverse to the proximal axis.

Although the invention herein has been described with reference to particular embodiments, it is to be understood that these embodiments are merely illustrative of the principles and applications of the present disclosure. It is therefore to be understood that numerous modifications may be made to the illustrative embodiments and that other arrange-

The invention claimed is:

1. An arthrodesis implant for joining a first bone and a second bone that form an articulable joint, comprising:
 a first elongate portion;
 a second elongate portion joined to the first elongate portion at a proximal end and a distal end of the arthrodesis implant,
 wherein the first elongate portion and second elongate portion each extend away from a plane and each other at the proximal and distal ends of the arthrodesis implant and extend toward the plane intermediate the proximal and distal ends so as to form a first and second space between the first and second elongate portions.

2. The implant of claim 1, wherein the plane intersects the proximal and distal ends of the arthrodesis implant.

3. The implant of claim 1, wherein the plane intersects the first and second spaces.

4. The implant of claim 1, wherein a longitudinal axis of the arthrodesis implant lies in the plane.

5. The implant of claim 3, wherein the first and second elongate portions are offset from each other in a direction parallel to the plane.

6. The implant of claim 1, wherein a maximum distance between the first and second elongate portions at the first space is perpendicular to the plane.

7. The implant of claim 1, wherein the first elongate portion has a first end section, a second end section, and a middle section, the first elongate portion intersecting the plane such that the first and second end sections are positioned at a first side of the plane and the middle section is positioned at a second side of the plane.

8. The implant of claim 7, wherein the second elongate portion has a first end section, a second end section, and a middle section, the second elongate portion intersecting the plane such that the first and second end sections thereof are positioned at the second side of the plane and the middle section is positioned at the first side of the plane.

9. The implant of claim 8, wherein the first end sections of the first and second elongate portions define the first space, the second end sections of the first and second elongate portions define the second space, and the middle sections of the first and second elongate portions define a third space.

10. The implant of claim 1, wherein the first and second elongate portions are moveable between a first state and a second state, the proximal and distal ends being further from each other in the second state than in the first state.

11. The implant of claim 10, wherein the first and second elongate portions are biased toward the first state.

12. The implant of claim 11, further comprising a removable clip configured to be positioned between the first and second elongate portions so as to hold the first and second elongate portions in the second state.

13. The implant of claim 1, wherein the first and second elongate portions each include a plurality of barbs extending outwardly therefrom.

14. An arthrodesis implant for joining a first bone and a second bone that form an articulable joint, comprising:
 a first elongate portion having a first end and a second end;
 a second elongate portion having a first end joined to the first end of the first elongate portion and a second end joined to the second end of the first elongate portion;
 wherein the first and second elongate portions curve away from each other at their respective first and second ends and curve towards each other and past each other at a region intermediate the first and second ends.

15. The implant of claim 14, wherein the first and second elongate portions define a first space, a second space, and a third space, the third space being located between the first and second spaces along a longitudinal axis of the arthrodesis implant.

16. The implant of claim 15, wherein the first and second elongate portions are moveable between a first state and a second state.

17. The implant of claim 16, wherein a first and second distance between the first and second elongate portions at the first and second spaces, respectively, are greater in the first state than in the second state.

18. The implant of claim 17, wherein a third distance between the first and second elongate portions at the third space is greater in the second state than in the first state.

19. The implant of claim 18, wherein the first and second elongate portions are offset from each other at the third space in a direction perpendicular to the longitudinal axis of the arthrodesis implant and perpendicular to the third distance.

20. The implant of claim 19, further comprising a removable clip configured to be positioned within the third space to maintain the first and second elongate portions in the second state.

* * * * *